United States Patent
Arikawa et al.

(10) Patent No.: US 11,453,896 B2
(45) Date of Patent: Sep. 27, 2022

(54) TRANSFORMED MICROORGANISM FOR PRODUCING PHA COPOLYMER COMPRISING 3HH MONOMER UNIT AT HIGH COMPOSITION RATE AND METHOD FOR PRODUCING PHA USING SAME

(71) Applicant: KANEKA CORPORATION, Osaka (JP)

(72) Inventors: Hisashi Arikawa, Takasago (JP); Shunsuke Sato, Takasago (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 16/927,229

(22) Filed: Jul. 13, 2020

(65) Prior Publication Data

US 2020/0340020 A1 Oct. 29, 2020

Related U.S. Application Data

(63) Continuation of application No. PCT/JP2019/001181, filed on Jan. 17, 2019.

(30) Foreign Application Priority Data

Jan. 17, 2018 (JP) .............................. JP2018-005998

(51) Int. Cl.
*C12P 7/625* (2022.01)
*C12N 9/10* (2006.01)

(52) U.S. Cl.
CPC ............ *C12P 7/625* (2013.01); *C12N 9/1029* (2013.01); *C12Y 203/01009* (2013.01)

(58) Field of Classification Search
CPC .......... C12P 7/62; C12P 7/625; C12N 9/1029; C12N 5/10; C12N 15/09; C12Y 203/01009
See application file for complete search history.

(56) References Cited

U.S. PATENT DOCUMENTS

| | | | |
|---|---|---|---|
| 4,393,167 | A | 7/1983 | Holmes et al. |
| 5,292,860 | A | 3/1994 | Shiotani et al. |
| 5,981,257 | A | 11/1999 | Fukui et al. |
| 2011/0091948 | A1 | 4/2011 | Murakami et al. |
| 2013/0071892 | A1 | 3/2013 | Fukui et al. |
| 2017/0009221 | A1 | 1/2017 | Arikawa et al. |

FOREIGN PATENT DOCUMENTS

| | | |
|---|---|---|
| EP | 0114086 A2 | 7/1984 |
| EP | 3 101 129 A1 | 12/2016 |
| JP | 57-150393 A | 9/1982 |
| JP | 59-220192 A | 12/1984 |
| JP | 5-093049 A | 4/1993 |
| JP | 7-265065 A | 10/1995 |
| JP | 10-108682 A | 4/1998 |
| JP | 2001-340078 A | 12/2001 |
| JP | 2008-29218 A | 2/2008 |
| JP | 2008-86238 A | 4/2008 |
| WO | WO 2009/145164 A1 | 12/2009 |
| WO | WO 2011/105379 A1 | 9/2011 |
| WO | WO 2015/115619 A1 | 8/2015 |
| WO | WO-2017068385 A1 * 4/2017 ..... C12Y 203/01009 |

OTHER PUBLICATIONS

International Search Report dated Apr. 23, 2019, in PCT/JP2019/001181, filed Jan. 17, 2019.
Y. Doi, S. Kitamura, H. Abe, Macromolecules, 28, pp. 4822-4823 (1995).
T. Fukui, Y. Doi, Journal of Bacteriology, vol. 179, No. 15, pp. 4821-4830 (Aug. 1997).
H. Arikawa, K. Matsumoto, Microb. Cell. Fact., 15, pp. 184 (2016).
Sato, Shunsuke et al., "Regulation of 3-hydroxyhexanoate composition in PHBH synthesized by recombinant Cupriavidus necator H16 from plant oil by using butyrate as a co-substrate", Journal of Bioscience and Bioengineering, 2015, vol. 120, No. 3, pp. 246-251, entire text.
T. Fukui, H. Abe, Y. Doi, Biomacromolecules, 3, pp. 618-624 (2002).
Q. Wang et al., Appl. Microbiol Biotechnol., 99, pp. 2593-2602 (2015).

(Continued)

*Primary Examiner* — Paul J Holland
(74) *Attorney, Agent, or Firm* — Oblon, McClelland, Maier & Neustadt, L.L.P.

(57) ABSTRACT

The present application provides: a transformed microorganism for producing a PHA copolymer containing 3HH monomer unit at a higher composition ratio, specifically, a transformed microorganism comprising a PHA synthase gene capable of synthesizing a PHA copolymer containing 3HH monomer unit and a gene encoding a protein having (R)-specific enoyl-CoA hydratase activity, characterized in that, in the transformed microorganism, the expression of a gene encoding at least one β-ketothiolase enzyme having thiolysis activity for β-keto-(C6) acyl-CoA (i.e., β-ketohexanoyl-CoA) is inhibited, thereby losing or reducing the enzyme activity; and a method for producing a PHA copolymer containing 3HH monomer unit, comprising a step of culturing the transformed microorganism.

13 Claims, No Drawings

Specification includes a Sequence Listing.

(56) References Cited

OTHER PUBLICATIONS

Lindenkamp, Nicole et al., "Impact of Multiple-β-Ketothiolase Deletion Mutations in Ralstonia eutropha H16 on the Composition of 3-Mercaptopropionic Acid-Containing Copolymers", Applied and Environmental Microbiology, 20ro,vol. 76, No. 16, pp. 5373-5382, table 3.
Extended European Search Report dated Nov. 5, 2021 in European Patent Application No. 19741727.2, 7 pages.
Jun Mifune, et al., "Engineering of Pha Operon on Cupriavidus Necator Chromosome for Efficient Biosynthesis of Poly(3-hydroxibutyrate-co-3-hydroxyhexanoate) from Vegetable Oil" Polymer Degradation and Stability, vol. 95, No. 8, XP027122897, Aug. 1, 2010, pp. 1305-1312.
Arikawa et al, "Impact of various β-ketothiolase genes on PHBHHx production in Cupriavidus necator H16 derivatives", *Applied Microbiology and Biotechnology* (2022) vol. 106, pp. 3021-3032.

\* cited by examiner

TRANSFORMED MICROORGANISM FOR PRODUCING PHA COPOLYMER COMPRISING 3HH MONOMER UNIT AT HIGH COMPOSITION RATE AND METHOD FOR PRODUCING PHA USING SAME

CROSS-REFERENCE TO RELATED APPLICATIONS

This application is a continuation of International Patent Application No. PCT/JP2019/001181, filed on Jan. 17, 2019, and claims priority to Japanese Patent Application No. 2018-005998, filed on Jan. 17, 2018, all of which are incorporated herein by reference in their entireties.

TECHNICAL FIELD

The present invention relates to: a transformed microorganism that produces a polyhydroxyalkanoate copolymer (hereinafter, occasionally referred to as a "PHA copolymer" or simply as "PHA") comprising 3-hydroxyhexanoic acid (hereinafter, occasionally referred to as "3HH") monomer unit at a high composition ratio (or rate), using oil(s) and fat(s) or fatty acid(s) as the raw material; and a method for producing a PHA copolymer using the aforementioned transformed microorganism.

BACKGROUND ART

Polyhydroxyalkanoate (PHA) is a polyester-type organic polymer produced by a wide variety of microorganisms. PHA is a thermoplastic polymer having biodegradability, which can be produced from a renewable resource used as a raw material. In view of the foregoing, an attempt has been made to industrially produce PHA as an environmentally conscious material or a biocompatible material and then to utilize the produced PHA in a variety of industries.

To date, it has been known that a large number of microorganisms accumulate PHA as an energy storage material in their cells. A typical example of the PHA may be poly-3-hydroxybutyric acid (hereinafter, occasionally referred to as "P(3HB)") that is a homopolymer of 3-hydroxybutyric acid (hereinafter, occasionally referred to as "3HB"). Since P(3HB) is a thermoplastic polymer that is biologically decomposed in the natural environment, it has been focused as an environmentally friendly plastic. However, P(3HB) is hard and fragile because of its high crystallinity, and thus, the practically applicable range thereof is limited. In order to widen the applicable range, it has been necessary to impart flexibility to P(3HB).

Hence, a PHA copolymer (hereinafter referred to as "P(3HB-co-3HV)") consisting of 3HB and 3-hydroxyvaleric acid (hereinafter referred to as "3HV") and a production method thereof have been developed (for example, Patent Literature 1 and Patent Literature 2). Since P(3HB-co-3HV) had higher flexibility than P(3HB), it was considered that the range of applications of P(3HB-co-3HV) would be extensive. In practice, however, an increased 3HV molar fraction in P(3HB-co-3HV) does not lead to desirable physical changes. In particular, the flexibility of P(3HB-co-3HV) has not been sufficiently improved in view of flexibility necessary for being processed in the form of, for example, films, sheets, or soft-type packaging containers. Accordingly, the application of this material is limited to hard-type molded products, such as shampoo bottles or disposable razor handles.

Also, a PHA copolymer comprising 3HB and 3HH (hereinafter, such copolymer is occasionally referred to as "P(3HB-co-3HH)") and a method for producing the same have been studied in order to further enhance PHA flexibility (Patent Literature 3 and Patent Literature 4). In these literatures, P(3HB-co-3HH) was produced by fermentation using a wild-type strain of Aeromonas caviae isolated from soil and fatty acid, such as oleic acid or palmitic acid, as a carbon source.

Physical properties of P(3HB-co-3HH) have also been studied (Non Patent Literature 1). In this study, A. caviae is cultured using, as a single carbon source, a fatty acid(s) containing 12 or more carbon atoms, and P(3HB-co-3HH) having various 3HH composition ratios is produced by fermentation. It was revealed that as the 3HH composition ratio increases in P(3HB-co-3HH), the hard and fragile properties seen in, for example, P(3HB) gradually change into more flexible properties superior to P(3HB-co-3HV) This suggests that changing a 3HH composition ratio of P(3HB-co-3HH) may promise application to a wide range of fields, because an extensive range of physical properties that are applicable to polymers of from hard to soft polymers can be imparted to P(3HB-co-3HH).

In addition, transformed microorganisms were produced by introducing a polyester synthase gene, the (R)-specific enoyl-CoA hydratase gene, or the like into the plasmid pJRD215 (ATCC 37533) to prepare a PHA synthase expression plasmid such as pJRDEE32 or pJRDEE32d13, and then transforming Cupriavidus necator (C. necator) used as a host with the PHA synthase expression plasmid, and the PHA productivity of the transformed microorganisms has been studied (Patent Literature 5 and Non Patent Literature 2). While the amount of the cells was as low as 4 g/l after culture, it was found that polymer productivity increased by improvement of cell culture conditions involving using plant oils and fats as carbon sources. For example, the amount of the cells increased by up to 45 g/l and the polymer content by up to 62.5%. Furthermore, it was also found that the 3HH composition ratio increased by up to 8.1 mol %. Thus, an attempt to improve a 3HH composition ratio or polymer productivity of P(3HB-co-3HH) by changing culture conditions have been made (Patent Literature 6).

There are also reports in which the 3HH composition ratio was improved by enhancing the expression of the (R)-specific enoyl-CoA hydratase gene (Patent Literature 7, Patent Literature 8, and Non Patent Literature 3). According to these reports, when a (R)-specific enoyl CoA hydratase gene is introduced into Cupriavidus necator having Aeromonas caviae-derived PHA synthase, or when the expression level of a (R)-specific enoyl CoA hydratase gene on the host chromosome is increased, the composition ratio of 3HH in P(3HB-co-3HH) produced using plant oil and fat as a raw material is improved by up to approximately 14 mol %.

Furthermore, it is also reported that a C. necator strain, in which the expression of a bktB gene encoding β-ketothiolase has been enhanced, produced P(3HB-co-3HH) polymers in which the 3HH composition ratio was improved by up to 13 mol %, using vegetable oil and butyric acid as carbon sources (see Non Patent Literature 4). It was also known that β-ketothiolase encoded by the bktB gene had activity of condensing (C4) butyryl CoA and (C2) acetyl CoA to generate β-keto-(C6) hexanoyl CoA that is a precursor of a 3HH monomer. Focusing on this condensation activity, an attempt to improve the composition ratio of 3HH in P(3HB-co-3HH) by enhancing the β-ketothiolase gene has been reported also in other publications (Non Patent Literature 5 and Non Patent Literature 6).

CITATION LIST

Patent Literature

Patent Literature 1: Japanese Patent Publication (Kokai) No. 57-150393 A (1982)
Patent Literature 2: Japanese Patent Publication (Kokai) No. 59-220192 A (1984)
Patent Literature 3: Japanese Patent Publication (Kokai) No. 5-93049A (1993)
Patent Literature 4: Japanese Patent Publication (Kokai) No. 7-265065 A (1995)
Patent Literature 5: Japanese Patent Publication (Kokai) No. 10-108682 A (1998)
Patent Literature 6: Japanese Patent Publication (Kokai) No. 2001-340078 A
Patent Literature 7: PCT International Publication No. WO2011/105379
Patent Literature 8: PCT International Publication No. WO2015/115619

Non Patent Literature

Non Patent Literature 1: Y. Doi, S. Kitamura, H. Abe, Macromolecules, 28, pp. 4822-4823 (1995)
Non Patent Literature 2: T. Fukui, Y. Doi, J. Bacteriol, 179, 15, pp. 4821-4830 (1997)
Non Patent Literature 3: H. Arikawa, K. Matsumoto, Microb. Cell. Fact., 15, pp. 184 (2016)
Non Patent Literature 4: S. Sato et al., J. Biosci. Bioeng., 120, pp. 246-251 (2015)
Non Patent Literature 5: T. Fukui, H. Abe, Y. Doi, Biomacromolecules, 3, pp. 618-624 (2002)
Non Patent Literature 6: Q. Wang et al., Appl. Microbiol. Biotechnol., 99, pp. 2593-2602 (2015)

SUMMARY OF INVENTION

Technical Problem

It is an object of the present invention to provide: a transformed microorganism that produces a PHA copolymer containing 3HH monomer unit at a higher composition ratio; and a method for producing a PHA copolymer, using oil(s) and fat(s) or fatty acid(s) (preferably, plant-derived oil(s) and fat(s) or fatty acid(s)) as the raw material, and also using the aforementioned transformed microorganism.

Solution to Problem

The present inventors have conducted intensive studies to solve the aforementioned technical problem, and as a result, the inventors have now found that the expression of a gene or genes encoding at least one or at least two β-ketothiolase enzymes with thiolysis activity for β-keto-(C6) acyl CoA (i.e., β-ketohexanoyl CoA) is inhibited, and thereby, the aforementioned enzyme activity is lost or reduced, so that a PHA copolymer containing 3HH monomer units at a higher composition ratio can be produced via fermentation, thereby completing the present invention.

Specifically, the present invention relates to a transformed microorganism comprising a PHA synthase gene capable of synthesizing a PHA copolymer containing 3HH monomer unit and a gene encoding a protein having (R)-specific enoyl-CoA hydratase activity, which is characterized in that, in the transformed microorganism, the expression of a gene encoding at least one or at least two β-ketothiolase enzymes having thiolysis activity for β-ketohexanoyl-CoA that is β-ketoacyl-CoA containing 6 carbon atoms, is inhibited, thereby losing or reducing the enzyme activity.

According to an embodiment of the present invention, the expression of the gene encoding a protein having (R)-specific enoyl-CoA hydratase activity is further enhanced in the transformed microorganism of the present invention.

According to an embodiment of the present invention, the expression of a PHA synthase gene capable of synthesizing a PHA copolymer containing 3HH monomer unit is further enhanced in the transformed microorganism of the present invention.

As used herein, the "inhibition of the expression" of a gene means that the activity of the above-described β-ketothiolase enzyme is lost or reduced, and inhibition of the expression includes removal of functions of the gene encoding the enzyme. Examples of the method of inhibiting the gene expression include, but are not particularly limited to, methods such as gene knockout utilizing the entire or partial disruption of a gene encoding the above-described β-ketothiolase enzyme (for example, genome editing techniques (e.g., CRISPR/Cas (e.g., Cas9) system, TALEN, etc.), gene disruption that utilizes homologous recombination techniques, gene disruption that utilizes transposon, etc.), reduction in transcription or translation efficiency of the gene, modification of a promoter region associated with transcription of the gene or modification of a ribosome binding sequence associated with translation of the gene, modification of a nucleotide sequence of a transcription region so as to make mRNA unstable, decomposition or cleavage of mRNA by RNA interference, and change in substrate specificity of the enzyme. In addition, drugs, proteins and the like that inhibit the activity of the enzyme may also be used.

As used herein, the "disruption" of a gene refers to, unless otherwise specified, a state in which an enzyme protein itself encoded by a gene encoding β-ketothiolase enzyme is disrupted by removal (or deletion) or cleavage of the nucleotide sequence of the gene, or by mutation, such as deletion, substitution, addition or insertion, of the nucleotide sequence of the gene.

As used herein, the term "reduction" in the activity of the above-described enzyme protein means a reduction in the activity so that the composition ratio of 3HH monomer unit in the PHA copolymer becomes higher than that in a control in which the enzyme activity is not reduced. Alternatively, the activity of the above-described enzyme protein is preferably lost, however, with regard to the relative activity of the enzyme protein to the activity (100%) of an intact protein, weak activity may remain, and it is, for example, 20% or less, 10% or less, 5% or less, 2% or less, or 1% or less, but is not limited thereto.

As used herein, the term "increase" or "enhancement" of the gene expression means that the expression level of the gene is increased or enhanced.

According to an embodiment of the present invention, the above-described microorganism is preferably a bacterium (also referred to as bacteria), is more preferably a bacterium belonging to the genus *Cupriavidus*, and is further preferably *Cupriavidus necator* (for example, *Cupriavidus necator* H16 strain).

According to an embodiment of the present invention, the above-described gene encoding β-ketothiolase is at least one gene selected from the group consisting of a *Cupriavidus necator* H16 strain-derived bktB gene or homologs thereof, and a *Cupriavidus necator* H16 strain-derived A1528 gene (Gene No. "H16_A1528") or homologs thereof.

As used herein, the term "homolog" used includes any of ortholog and paralog. The homolog is a gene group encoding proteins having β-ketothiolase activity possessed by homogeneous or heterogeneous microorganisms. The terms "ortholog" and "paralog" have academically commonly used meanings. Specifically, the term "ortholog" indicates a homolog (homologue) diverged during speciation, which is a gene group having homologous function that is present in different microorganisms. On the other hand, the term "paralog" indicates a homolog generated as a result of gene duplication.

According to an embodiment of the present invention, the above-described gene encoding β-ketothiolase is a *Cupriavidus necator* H16 strain-derived bktB gene or a homolog of the bktB gene derived from bacteria belonging to the genus *Cupriavidus* (for example, *Cupriavidus necator*), or a *Cupriavidus necator* H16 strain-derived A1528 gene or a homolog of the A1528 gene derived from bacteria belonging to the genus *Cupriavidus* (for example, *Cupriavidus necator*), or both of them.

According to an embodiment of the present invention, the above-described bktB gene comprises the nucleotide sequence as shown in (or represented by) SEQ ID NO: 7, or a nucleotide sequence having 85% or higher sequence identity with the aforementioned nucleotide sequence, and the A1528 gene comprises the nucleotide sequence as shown in SEQ ID NO: 8, or a nucleotide sequence having 85% or higher sequence identity with the aforementioned nucleotide sequence.

The present invention further relates to a method for producing a PHA copolymer containing 3HH monomer unit, comprising a step of culturing the above-described transformed microorganism using a carbon source comprising oil(s) and fat(s) or fatty acid(s) (preferably, plant-derived oil(s) and fat(s) or fatty acid(s)) and a step of recovering a PHA copolymer containing 3HH monomer unit. The PHA copolymer is preferably P(3HB-co-3HH) (another name: poly(3-hydroxybutyrate-co-3-hydroxyhexanoate)).

The present description includes the content disclosed in Japanese Patent Application No. 2018-005998, from which the present application claims priority.

Effect of Invention

According to the present invention, a transformed microorganism producing a PHA copolymer containing 3HH monomer unit at a higher composition ratio may be provided. In addition, through culturing the transformed microorganism, it is possible to produce a PHA copolymer containing 3HH monomer unit at a higher composition ratio by fermentation. Such a PHA copolymer has an advantage in that it has improved flexibility.

DESCRIPTION OF EMBODIMENTS

Hereinafter, the present invention will be described in more detail.
1. Transformed Microorganism Producing PHA Copolymer Containing 3HH Monomer Unit According to one aspect, the present invention provides a transformed microorganism comprising a PHA synthase gene capable of synthesizing a PHA copolymer containing 3HH monomer unit and a gene encoding a protein having (R)-specific enoyl-CoA hydratase activity, characterized in that, in the transformed microorganism, the expression of a gene(s) encoding at least one or at least two β-ketothiolase enzymes having thiolysis activity for β-keto-(C6) acyl-CoA (i.e., β-ketohexanoyl-CoA), is inhibited, thereby losing or reducing the enzyme activity. The transformed microorganism is capable of producing a PHA copolymer containing 3HH monomer unit at a higher composition ratio than a control microorganism in which the above-described enzyme activity is neither lost nor reduced.

As used herein, the term "higher composition ratio" regarding the 3HH monomer unit means that the composition ratio of 3HH monomer unit in a PHA copolymer produced by β-ketothiolase enzyme having thiolysis activity for β-ketohexanoyl-CoA is higher compared with a control microorganism in which the β-ketothiolase enzyme is intact (namely, in a native or natural state), or with a control microorganism in which the expression of the gene encoding the β-ketothiolase enzyme is not inhibited.

As used herein, the term "β-ketothiolase enzyme" refers to an enzyme that catalyzes the reaction in which β-ketoacyl-CoA causes thiolysis (thiol cleavage) in the presence of co-enzyme A in the 13 oxidation of fatty acid so as to generate acetyl-CoA and fatty acyl-CoA that has become 2 carbons shorter than before. In the present invention, losing or reducing the activity of the β-ketothiolase enzyme enables to suppress decomposition of β-ketohexanoyl-CoA, so that the composition ratio of 3HH monomer unit in the produced PHA copolymer increases.

As used herein, the term "PHA synthase" refers to an enzyme that biosynthesizes a polyhydroxyalkanoate, and it can polymerize two or more (R)-3-hydroxyacyl-CoA species including (R)-3-hydroxyhexanoyl-CoA to generate PHA copolymers containing 3HH monomer unit.

As used herein, the term "protein having (R)-specific enoyl-CoA hydratase activity" refers to a protein having enzyme activity to convert enoyl-CoA that is an intermediate of fatty acid β oxidation system to (R)-3-hydroxyacyl-CoA that is a source for PHA monomers.

The transformed microorganism of the present invention has the following characteristics.
(1) The transformed microorganism comprises a PHA synthase gene capable of synthesizing a PHA copolymer containing 3HH monomer unit and a gene encoding a protein having (R)-specific enoyl-CoA hydratase activity.
(2) Preferably, the expression of the gene encoding a protein having (R)-specific enoyl-CoA hydratase activity is enhanced. By such enhancement, the composition ratio of 3HH monomer in the PHA copolymer containing the 3HH monomer unit becomes higher than that in the case of not enhancing the expression. The present invention is characterized in that the aforementioned composition ratio can be further enhanced, unexpectedly, by adding the property in (4) below to the property in this item.
(3) Preferably, the expression of the PHA synthase gene capable of synthesizing a PHA copolymer containing 3HH monomer unit is enhanced.
(4) The microorganism has an ability to produce a PHA copolymer containing 3HH monomer unit at a high composition ratio, which is characterized in that the expression of a gene(s) encoding at least one or at least two β-ketothiolase enzymes having thiolysis activity for β-keto-(C6) acyl-CoA (i.e., β-ketohexanoyl-CoA) is inhibited, thereby losing or reducing the enzyme activity. Herein, the "reduction" of the above-described enzyme activity means a reduction in the activity, by which the composition ratio of 3HH monomer unit in the PHA copolymer becomes higher than a control in which the enzyme activity is not reduced, as described above.
(5) By having the above-described properties (1) to (4), the transformed microorganism of the present invention may have an ability to produce a PHA copolymer containing 3HH monomer unit at a high composition ratio.

As described above, the microorganism serving as an original strain (also referred to as a "parent strain") that inhibits the expression of the above-described gene is not particularly limited, as long as it is a microorganism comprising a PHA synthase gene capable of synthesizing a PHA copolymer containing 3HH monomer unit and a gene encoding a protein having (R)-specific enoyl-CoA hydratase activity. Examples of such a microorganism may include not only wild-type strains originally having the above-described PHA synthase gene and the gene encoding a protein having (R)-specific enoyl-CoA hydratase activity, but also mutant strains obtained by subjecting the wild-type strains to artificial mutation treatments, and recombinant microorganism strains into which a foreign PHA synthase gene and/or a foreign gene encoding a protein having (R)-specific enoyl-CoA hydratase activity have been introduced according to genetic engineering methods.

Examples of the microorganism usable in the present invention include molds, yeasts, bacteria, Actinomycetes, cyanobacteria, and archaea, and among these, bacteria are preferable. Preferred examples of the bacteria include bacteria belonging to the genus *Ralstonia*, the genus *Cupriavidus*, the genus *Wautersia*, the genus *Aeromonas*, the genus *Escherichia*, the genus *Alcaligenes*, the genus *Pseudomonas*, etc. From the viewpoint of safety and productivity, bacteria belonging to the genus *Ralstonia*, the genus *Cupriavidus*, the genus *Aeromonas*, or the genus *Wautersia* are more preferable; bacteria belonging to the genus *Cupriavidus* or the genus *Aeromonas* are more preferable; bacterium belonging to the genus *Cupriavidus* are far more preferable; and *Cupriavidus necator* is particularly preferable.

With regard to the transformed microorganism of the present invention, the above-described target gene group (namely, a PHA synthase gene, a gene encoding a protein having (R)-specific enoyl-CoA hydratase activity, and a gene encoding β-ketothiolase enzyme) can be modified, so that the target gene group can have the above-described properties (1) to (5), with respect to the above-exemplified microorganisms, or among the above-exemplified microorganisms. The present modification will be further described below.

As used herein, with respect to the microorganism having PHA synthase gene, the wording "capable of synthesizing a PHA copolymer containing 3HH monomer unit" does not mean that the microorganism has to be able to synthesize the PHA copolymer containing 3HH monomer unit under all culture conditions, and, the wording means that even if the microorganism is capable of synthesizing the PHA copolymer containing 3HH monomer unit under specific culture conditions, that may be enough. For example, the strain described in Comparative Example 1 described later (i.e., KNK005dZ) does not synthesize the PHA copolymer containing 3HH monomer unit under culture conditions in which fructose is used as a single carbon source, but this strain is able to synthesize the PHA copolymer containing 3HH monomer unit under culture conditions containing oil(s) and fat(s) or fatty acid(s) as the carbon source. As such, in the present invention, the aforementioned microorganism corresponds to the "microorganism having a PHA synthase gene capable of synthesizing a PHA copolymer containing 3HH monomer unit."

When the microorganism having a PHA synthase gene capable of synthesizing a PHA copolymer containing 3HH monomer unit is a recombinant microorganism strain into which a foreign PHA synthase gene has been introduced according to genetic engineering methods, the foreign PHA synthase gene is not particularly limited, as long as it is a gene having the function of incorporating 3HH and producing the PHA copolymer containing 3HH monomer unit. Examples of such a PHA synthase gene include, but are not limited to: an *Aeromonas caviae*-derived PHA synthase gene encoding enzyme having the amino acid sequence as shown in SEQ ID NO: 1; or PHA synthase genes encoding polypeptides having sequence identity of 85% or higher, preferably 90% or higher, more preferably 95% or higher, and particularly preferably 99% or higher to the aforementioned amino acid sequence, and having activity of synthesizing a PHA copolymer containing 3HH monomer unit. Among these genes, PHA synthase genes capable of synthesizing P(3HB-co-3HH) as the PHA copolymer containing 3HH monomer unit are preferable, and among them, for example, a PHA synthase gene encoding PHA synthase comprising the amino acid sequence as shown in SEQ ID NO: 2 is more preferable.

Moreover, when the above-described microorganism is a recombinant microorganism strain into which a foreign gene encoding a protein having (R)-specific enoyl-CoA hydratase activity has been introduced according to genetic engineering methods, examples of the foreign gene encoding a protein having (R)-specific enoyl-CoA hydratase activity include, but are not limited to: an *Aeromonas caviae*-derived (R)-specific enoyl-CoA hydratase gene encoding an enzyme having the amino acid sequence as shown in SEQ ID NO: 3; *Cupriavidus necator*-derived (R)-specific enoyl-CoA hydratase genes encoding enzymes having the amino acid sequences as shown in SEQ ID NO: 4 and SEQ ID NO: 5; a *Yarrowia lipolytica*-derived Multifunctional enzyme type 2 (MFE2) gene encoding an enzyme having the amino acid sequence as shown in SEQ ID NO: 6; and genes encoding proteins having sequence identity of 85% or higher, preferably 90% or higher, more preferably 95% or higher, and particularly preferably 99% or higher to the amino acid sequence as shown in each of SEQ ID NOs: 3 to 6, and also having (R)-specific enoyl-CoA hydratase activity.

In order to enhance the expression of a gene encoding a protein having (R)-specific enoyl-CoA hydratase activity, for example, as described in PCT International Publication No. WO2015/115619, expression regulatory sequences for enhancing the expression of the gene (a promoter sequence and/or an SD sequence) may be modified.

In the present invention, the microorganism serving as an origin strain is most preferably a recombinant prokaryotic microorganism strain prepared by introducing an *Aeromonas caviae*-derived PHA synthase gene into *Cupriavidus necator*.

Next, with respect to the above-described microorganism, inhibition of the expression of a gene encoding β-ketothiolase having thiolysis activity for β-keto-(C6) acyl-CoA (i.e., β-ketohexanoyl-CoA) will be described.

The target gene whose expression is inhibited may be a gene encoding β-ketothiolase having thiolysis activity for β-keto-(C6) acyl-CoA wherein the β-ketothiolase may simultaneously have thiolysis activity for β-ketoacyl-CoA having other carbon number rather than 6. For example, the β-ketothiolase may have thiolysis activity for β-keto-(C4-C6) acyl-CoA, or thiolysis activity for β-keto-(C4-C18) acyl-CoA, or thiolysis activity for β-keto-(C6-C20) acyl-CoA, but the examples of the β-ketothiolase are not limited thereto.

A transformed microorganism, which is obtained by performing inhibition of the gene expression on a microorganism comprising the above-described PHA synthase gene and the gene encoding a protein having (R)-specific enoyl-CoA hydratase activity, is able to produce a PHA copolymer containing 3HH monomer unit at a higher composition ratio.

In general, oil(s) and fat(s) or fatty acid(s) (preferably, plant-derived oil(s) and fat(s) or fatty acid(s)) are metabolized in microorganisms by β oxidation and are decomposed to (C2) acyl-CoA (namely, acetyl-CoA). In the case of a microorganism having a gene encoding a protein having (R)-specific enoyl-CoA hydratase activity, during the β oxidation, a moiety of 2-enoyl-CoA having a carbon number of C6 that is an intermediate metabolite of the β oxidation is converted to (R)-3-hydroxy-(C6) acyl-CoA that is a precursor of the 3HH monomer unit. According to the present invention, the expression of the above-described gene is inhibited, so that decomposition of the intermediate metabolite having a carbon number of C6 is suppressed during the β oxidation, in the case of using oil(s) and fat(s) or fatty acid(s) as the carbon source. As a result, it is presumed that the amount converted to (R)-3-hydroxy-(C6) acyl-CoA would increase, and that the composition ratio of 3HH monomer unit in PHA copolymers as the finally synthesized product becomes high.

On the other hand, it is not industrially favorable to destroy a β-ketoacyl-CoA gene to such an extent that the amount of the PHA copolymer produced is significantly reduced, in improving the composition ratio of the 3HH monomer unit. Thus, taking into consideration the produced PHA amount-reducing rate and the 3HH composition ratio-increasing rate caused by disruption of the β-ketoacyl-CoA gene, as the product of these rates increases, it is more preferable. For example, in a case where the amount of PHA produced is reduced to a half (½) and the 3HH composition ratio is increased to 1.4 times, the product (i.e., produced PHA amount-reducing rate×3HH composition ratio-increasing rate) becomes 0.7. In the present invention, the value of the produced PHA amount-reducing rate×the 3HH composition ratio-increasing rate under culture conditions described in Examples is preferably 0.65 or more, more preferably 0.75 or more, far more preferably 0.85 or more, still far more preferably 0.95 or more, and most preferably 1 or more, but the value is not limited thereto. It is to be noted that the term "produced PHA amount-reducing rate" refers to the ratio of the production amount of the PHA copolymer, compared with a transformed microorganism in which β-ketothiolase enzyme having thiolysis activity for β-ketohexanoyl-CoA is intact, or with a transformed microorganism in which the expression of a gene encoding the β-ketothiolase enzyme is not inhibited.

On the other hand, the term "3HH composition ratio-increasing rate" refers to the ratio of the 3HH composition ratio in the PHA copolymer, compared with a transformed microorganism, in which β-ketothiolase enzyme having thiolysis activity for β-ketohexanoyl-CoA is intact, or with a transformed microorganism, in which the expression of a gene encoding the β-ketothiolase enzyme is not inhibited. The 3HH composition ratio-increasing rate is a value that is greater than 1. The 3HH composition ratio-increasing rate is preferably 1.2 or more, more preferably 1.5 or more, and further preferably 1.8 or more, but the 3HH composition ratio-increasing rate is not limited thereto, as long as it is a value greater than 1.

In order to specifically lose or reduce β-ketothiolase activity, for example, the enzyme gene can be completely deleted, or a completely different gene such as drug resistance gene may be inserted into the sequence of the enzyme gene, or a portion of the sequence of the enzyme gene (preferably, a region associated with the enzyme activity) can be deleted or can be subjected to substitution with, or addition or insertion of a completely different DNA sequence. As long as the activity is lost or reduced, however, any possible types of expression inhibition may be carried out. Among the expression inhibitions, examples of the gene disruption manipulation include a homologous recombination techniques using a vector comprising a gene or DNA for disruption, techniques utilizing transposon, and the like (see below). Alternatively, as other disruption methods, known techniques, such as genome editing techniques using CRISPR/Cas (for example, Cas9) system or TALEN to disrupt target genes (Y. Wang et al., ACS Synth Biol. 2016, 5(7): 721-732; Bogdanove and Voytas, Science, 333: 1843-1846, 2011; Jinek, et al., Science, 337: 816-821, 2012; Shalem, et al., Science, 343: 84-87, 2014; and Wang, et al., Science, 343: 80-84, 2014), may be adopted. For example, according to the CRISPR/Cas9 system, guide RNA (gRNA) has a sequence capable of binding to a part of the nucleotide sequence of a β-ketothiolase gene to be disrupted, and has a role in guiding Cas9 to the target. In addition, the transcription and/or translation efficiency of the gene or the stability of mRNA is decreased by performing mutations such as deletion, substitution, addition, insertion, etc. of nucleotide sequences around the gene, so that the enzyme activity may be lost or reduced.

The above-described gene whose expression is inhibited is not particularly limited, as long as it is a gene encoding β-ketothiolase having thiolysis activity for β-keto-(C6) acyl-CoA. Examples of such a gene may include a *Cupriavidus necator* H16 strain-derived bktB gene comprising the nucleotide sequence as shown in SEQ ID NO: 7, or a bktB gene homolog having sequence identity of 85% or higher, preferably 90% or higher, more preferably 95% or higher, and particularly preferably 99% or higher, to the aforementioned nucleotide sequence. Other examples may include a *Cupriavidus necator* H16 strain-derived gene of the gene locus H16 A1528, comprising the nucleotide sequence as shown in SEQ ID NO: 8 (hereinafter, occasionally referred to as "A1528 gene"), or A1528 gene homologs having sequence identity of 85% or higher, preferably 90% or higher, more preferably 95% or higher, and particularly preferably 99% or higher, to the aforementioned nucleotide sequence. On the other hand, examples of a gene whose expression is inhibited (for example, which is disrupted) in Comparative Examples described later include: a phaA gene comprising the nucleotide sequence as shown in SEQ ID NO: 9 that is a gene encoding β-ketothiolase without thiolysis activity for β-keto-(C6) acyl-CoA; phaA gene homologs having sequence identity of 85% or higher, preferably 90% or higher, more preferably 95% or higher, and particularly preferably 99% or higher, to the aforementioned nucleotide sequence; a gene of the gene locus H16 A0462, comprising the nucleotide sequence as shown in SEQ ID NO: 10 that is another β-ketothiolase gene (hereinafter, occasionally referred to as "A0462 gene"); or A0462 gene homologs having sequence identity of 85% or higher, preferably 90% or higher, more preferably 95% or higher, and particularly preferably 99% or higher, to the aforementioned nucleotide sequence (see Table 1).

Moreover, in the above-described Non Patent Literature 3, it has been reported that P(3HB-co-3HH) comprising 3HH at a higher composition ratio may be produced using oil(s) and fat(s) or fatty acid(s) (preferably, plant-derived oil(s) and fat(s) or fatty acid(s)) as a carbon source, by introducing a (R)-specific enoyl-CoA hydratase gene into a *Cupriavidus necator* strain, into which a PHA synthase gene capable of incorporating a 3HH monomer has been introduced, or by enhancing the expression of a (R)-specific enoyl-CoA hydratase gene that is originally possessed by the strain. As described above, in addition to the above-described inhibition of the gene expression, additional introduction of a gene encoding a protein having (R)-specific enoyl-CoA hydratase activity, or enhancement of the expression of the existing gene may also be carried out in the transformed microorganism of the present invention. According to the additional introduction of the gene encoding a protein having (R)-specific enoyl-CoA hydratase activity and/or the enhancement of the expression of the existing gene, the synthetic pathway of the aforementioned (R)-3-hydroxy-(C6) acyl-CoA is enhanced or is made efficient, so that the composition ratio of 3HH monomer unit in the produced PHA copolymer is more improved.

Furthermore, in addition to the above-described inhibition of the gene expression, additional introduction of a PHA synthase gene capable of incorporating a 3HH monomer or enhancement of the expression of the existing gene may be carried out. According to the additional introduction of a PHA synthase gene capable of incorporating a 3HH monomer and/or the enhancement of the expression of the existing gene, incorporation of (R)-3-hydroxyacyl-CoA with increased conversion amount into P(3HB-co-3HH) is enhanced or is made efficient, so that the composition ratio of 3HH monomer unit in the produced PHA copolymer becomes high.

When a foreign gene is introduced into the transformed microorganism of the present invention, the introduced gene may be present on the chromosome of the microorganism serving as a host, or on the DNA of a plasmid, a megaplasmid or the like. From the viewpoint of retaining the introduced gene, the foreign gene is preferably present on the chromosome of the microorganism or on a megaplasmid, and is more preferably present on the chromosome of the microorganism. In addition, when the expression level of the gene originally possessed by the microorganism serving as a host is to be increased, the expression level of the gene may be increased by performing a substitution, deletion or addition on a nucleotide sequence located upstream of the gene.

The method of site-specifically substituting or inserting any DNA on the DNA possessed by the microorganism, or the method of deleting any site of the DNA possessed by the microorganism is well known to a person skilled in the art, and these methods may be used upon production of the transformed microorganism of the present invention. Examples of the representative methods include, but are not particularly limited to, a method of utilizing transposon and the mechanism of homologous recombination (Ohman et al., J. Bacteriol., vol. 162: p. 1068 (1985)), a method of using, as principles, site-specific incorporation caused by homologous recombination mechanism and deletion caused by homologous recombination at the second step (Noti et al., Methods Enzymol., vol. 154, p. 197 (1987)), and a method of allowing a *Bacillus subtilis*-derived sacB gene to coexist with the microorganism and then easily isolating a microorganism strain, in which the gene is deleted by homologous recombination at the second step, as a sucrose-added medium-resistant strain (Schweizer, Mol. Microbiol., vol. 6, p. 1195 (1992); Lenz et al., J. Bacteriol., vol. 176, p. 4385 (1994)). Moreover, examples of the method of introducing a vector into cells include, but are not particularly limited to, calcium chloride method, electroporation method, polyethylene glycol method, spheroplast method, and the like.

With regard to gene cloning or a genetic recombination technique, the techniques described in Sambrook, J. et al., Molecular Cloning, A Laboratory Manual, Cold Spring Harbor Laboratory Press (1989 or 2001), etc. may be utilized.

The promoters used to express the above-described various types of genes are not particularly limited. Examples of the promoter that can be used herein include *Cupriavidus necator* phaC1 gene promoter and phaP1 gene promoter, *Escherichia coli*-derived lac promoter, lacUV5 promoter, trc promoter, tic promoter and tac promoter, and a lacN17 promoter having an artificially produced *Escherichia coli*-derive modified nucleotide sequence as shown in SEQ ID NO: 11.

2. Method for Producing PHA Copolymer

A PHA copolymer can be produced by a method comprising culturing the transformed microorganism of the present invention to produce a PHA copolymer, and then recovering the obtained PHA copolymer.

In the production of a PHA copolymer according to the present invention, the above-described transformed microorganism is preferably cultured in a medium containing a carbon source, a nitrogen source, which is a nutrient source other than the carbon source, inorganic salts, and other organic nutrient sources.

As the carbon source, any type of carbon source may be used, as long as it is a carbon source containing plant oil(s) and fat(s) or fatty acid(s), which can be assimilated by the transformed microorganism of the present invention. Preferred examples of such a carbon source include: oils and fats, such as palm oil, palm kernel oil, corn oil, coconut oil, olive oil, soybean oil, rape seed oil and Jatropha oil, or fractionated oils thereof; and fatty acids, such as lauric acid, oleic acid, stearic acid, palmitic acid and myristic acid, or derivatives thereof.

Examples of the nitrogen source include: ammonia; ammonium salts such as, ammonium chloride, ammonium sulfate and ammonium phosphate; and peptone, meat extract, and yeast extract. Examples of such inorganic salts include potassium dihydrogen phosphate, disodium hydrogen phosphate, magnesium phosphate, magnesium sulfate, and sodium chloride. Examples of the other organic nutrient sources include: amino acids, such as glycine, alanine, serine, threonine, and proline; and vitamins, such as vitamin B1, vitamin B12, and vitamin C.

Conditions for culturing the transformed microorganism of the present invention, such as culture temperature, culture time, pH upon culture, and medium, may be conditions that are generally used in the culture of a host microorganism, such as the genus *Ralstonia*, the genus *Cupriavidus*, the genus *Wautersia*, the genus *Aeromonas*, the genus *Escherichia*, the genus *Alcaligenes*, or the genus *Pseudomonas*.

The type of the PHA copolymer produced in the present invention is not particularly limited, as long as it is a PHA copolymer containing 3HH monomer unit. A PHA copolymer obtained by polymerizing one or more monomers selected from among 2-hydroxy-(C4-C16) alkanoic acid, 3-hydroxy-(C4-C16) alkanoic acid (excluding 3HH) and 4-hydroxy-(C4-C16) alkanoic acid, with 3HH, is preferable; and P(3HB-co-3HH) that is a copolymer of 3-hydroxybutyric acid with 3-hydroxyhexanoic acid is more preferable. Besides, the type of the PHA copolymer produced may be appropriately selected depending on purposes, such as the type of a PHA synthase gene possessed by a microorganism used or the type of a PHA synthase gene introduced separately, the type of a metabolic gene associated with the synthesis thereof, and culture conditions.

In the present invention, the recovery of a PHA copolymer from the cells after the culture of the transformed microorganism is not particularly limited, and the recovery of the PHA copolymer may be carried out, for example, by the following methods. After completion of the culture, the cells are separated from the culture broth using a centrifuge or the like, and the cells are washed with distilled water, methanol or the like, and are then dried. From the dried cells, a PHA copolymer is extracted using an organic solvent such as chloroform. From the organic solvent solution containing the PHA copolymer, the cell components are removed by filtration or the like, and a poor solvent such as methanol or hexane is added to the filtrate, so that the PHA copolymer is precipitated. Further, the supernatant is removed by filtration or centrifugation, and the residue is then dried to recover the PHA copolymer.

The composition (mol %) of monomers including 3HH in the obtained PHA copolymer may be analyzed, for example, by (capillary) gas chromatography or nuclear magnetic resonance.

EXAMPLES

The present invention will be described in detail by the following examples. However, these examples are not intended to limit the scope of the present invention. Besides, the genetic manipulation, as a whole, can be carried out as described in Molecular Cloning (Cold Spring Harbor Laboratory Press (1989 or 2001)). In addition, enzymes, cloning hosts, and the like, which are used in the genetic manipulation, can be purchased from market suppliers, and can be used in accordance with instructions provided from the suppliers. The types of enzymes are not particularly limited, as long as they can be used for genetic manipulation.

A KNK005ΔphaZ1,2,6 strain (hereinafter, occasionally referred to as "KNK005dZ strain") used in the following Production Examples, Examples and Comparative Examples is a transformed microorganism, in which an *Aeromonas caviae*-derived PHA synthase gene (a gene encoding PHA synthase having the amino acid sequence as shown in SEQ ID NO: 2) is introduced onto the chromosome of a *Cupriavidus necator* H16 strain, and a phaZ1,2,6 gene as a PHA-degrading enzyme on the chromosome is deleted. This transformed microorganism can be produced in accordance with the method described in PCT International Publication No. WO 2014/065253. In addition, a KNK005 trc-phaJ4b/ΔphaZ1,2,6 strain (hereinafter, occasionally referred to as "KNK005dZ/trc-J4b strain") is a transformed microorganism, in which the expression of a (R)-specific enoyl-CoA hydratase gene on the chromosome of the KNK005ΔphaZ1,2,6 strain is enhanced. This transformed microorganism can be produced in accordance with the method described in PCT International Publication No. WO 2015/115619. Specifically, a promoter sequence or a Shine-Dalgarno (SD) sequence serving as a regulatory sequence of the gene is partly modified (deleted, substituted, added, or inserted), or these sequences are substituted with a promoter sequence or an SD sequence derived from other bacteria, so that the expression of the above-described gene can be enhanced. The method of enhancing gene expression is not limited thereto, and the gene expression can also be enhanced by further introducing a similar gene or a gene encoding an enzyme having similar activity into the strain.

(Production Example 1) Production of KNK005dZ/dphaA Strain

At the onset, a plasmid for gene disruption was produced. The production was carried out as follows.

According to PCR using synthetic oligo DNA, a DNA fragment (SEQ ID NO: 12) comprising nucleotide sequences upstream and downstream of a phaA structural gene was obtained. The obtained DNA fragment was digested with the restriction enzyme SwaI. This DNA fragment was ligated with the vector pNS2X-sacB described in Japanese Patent Publication (Kokai) No. 2007-259708 A, which had also been digested with SwaI, using DNA ligase (Ligation High (manufactured by Toyobo Co., Ltd.)), so as to produce the plasmid vector for gene disruption pNS2X-sacB+phaAUD having nucleotide sequences upstream and downstream of the phaA structural gene.

Subsequently, using the plasmid vector for gene disruption pNS2X-sacB+phaAUD, a KNK005dZ/dphaA strain as a gene-disrupted strain was produced as follows.

The *Escherichia coli* S17-1 strain (ATCC47055) was transformed with the plasmid vector for gene disruption pNS2X-sacB+phaAUD, and the obtained transformed microorganism was subjected to a mixed culture with the KNK005dZ strain on Nutrient Agar Medium (manufactured by Difco), so that conjugation transfer was carried out.

The obtained culture broth was seeded (or inoculated) on a 250 mg/L kanamycin-containing Simmons' agar medium (2 g/L sodium citrate, 5 g/L sodium chloride, 0.2 g/L magnesium sulfate heptahydrate, 1 g/L ammonium dihydrogen phosphate, 1 g/L dipotassium hydrogen phosphate, 15 g/L agar, pH 6.8), and strains that had grown on the agar medium were selected, thereby obtaining a strain, in which the plasmid had been incorporated onto the chromosome of the KNK005dZ strain. This strain was cultured for two generations in Nutrient Broth Medium (manufactured by Difco), and the culture was then diluted and applied onto Nutrient Agar Medium supplemented with 15% sucrose. The growing strains were obtained as strains from which the plasmid had been removed. Furthermore, according to analyses using PCR and DNA sequencer, a single strain, in which the region from the start codon to the stop codon of the phaA structural gene on the chromosome was deleted, was isolated. This gene-disrupted strain was named "KNK005dZ/dphaA strain." The obtained KNK005dZ/dphaA strain is a strain, in which the region from the start codon to the stop codon of each of the phaZ1 gene and the phaZ6 gene on the chromosome of the *Cupriavidus necator* H16 strain was deleted, the region from the 16th codon to the stop codon of the phaZ2 gene was further deleted, a gene encoding PHA synthase having the amino acid sequence as shown in SEQ ID NO: 2 was introduced onto the chromosome, and the region from the start codon to the stop codon of the phaA structural gene was deleted.

(Production Example 2) Production of KNK005dZ/dbktB Strain

At the onset, a plasmid for gene disruption was produced. The production was carried out as follows.

According to PCR using synthetic oligo DNA, a DNA fragment (SEQ ID NO: 13) comprising nucleotide sequences upstream and downstream of a bktB structural gene was obtained. The obtained DNA fragment was digested with the restriction enzyme SwaI. This DNA fragment was ligated with the vector pNS2X-sacB described in Japanese Patent Publication (Kokai) No. 2007-259708 A, which had also been digested with SwaI, using DNA ligase (Ligation High (manufactured by Toyobo Co., Ltd.)), so as to produce the plasmid vector for gene disruption pNS2X-sacB+bktBUD having nucleotide sequences upstream and downstream of the bktB structural gene.

Subsequently, using the plasmid vector for gene disruption pNS2X-sacB+bktBUD, and also using the KNK005dZ strain as a parent strain, a KNK005dZ/dbktB strain was produced as a gene-disrupted strain by the same method as that described above.

The obtained KNK005dZ/dbktB strain is a strain, in which the region from the start (or initiation) codon to the stop (or termination) codon of each of the phaZ1 gene and the phaZ6 gene on the chromosome of the *Cupriavidus necator* H16 strain was deleted, the region from the 16th codon to the stop codon of the phaZ2 gene was further deleted, a gene encoding PHA synthase having the amino acid sequence as shown in SEQ ID NO: 2 was introduced onto the chromosome, and the region from the start codon to the stop codon of the bktB structural gene was further deleted.

(Production Example 3) Production of KNK005dZ/dA1528 Strain

At the onset, a plasmid for gene disruption was produced. The production was carried out as follows.

According to PCR using synthetic oligo DNA, a DNA fragment (SEQ ID NO: 14) comprising nucleotide sequences upstream and downstream of an A1528 structural gene was obtained. The obtained DNA fragment was digested with the restriction enzyme SwaI. This DNA fragment was ligated with the vector pNS2X-sacB described in Japanese Patent Publication (Kokai) No. 2007-259708 A, which had also been digested with SwaI, using DNA ligase (Ligation High (manufactured by Toyobo Co., Ltd.)), so as to produce the plasmid vector for gene disruption pNS2X-sacB+A1528UD having nucleotide sequences upstream and downstream of the A1528 structural gene.

Subsequently, using the plasmid vector for gene disruption pNS2X-sacB+A1528UD, and also using the KNK005dZ strain as a parent strain, a KNK005dZ/dA1528 strain was produced as a gene-disrupted strain by the same method as that described above.

The obtained KNK005dZ/dA1528 strain is a strain, in which the region from the start codon to the stop codon of each of the phaZ1 gene and the phaZ6 gene on the chromosome of the *Cupriavidus necator* H16 strain was deleted, the region from the 16th codon to the stop codon of the phaZ2 gene was further deleted, a gene encoding PHA synthase having the amino acid sequence as shown in SEQ ID NO: 2 was introduced onto the chromosome, and the region from the start codon to the stop codon of the A1528 structural gene was further deleted.

(Production Example 4) Production of KNK005dZ/dbktdB/dA1528 Strain

Using the plasmid vector for gene disruption pNS2X-sacB+A1528UD produced in Production Example 3, and also using the KNK005dZ/dbktB strain produced in Production Example 2 as a parent strain, a KNK005dZ/dbktB/dA1528 strain was produced as a gene-disrupted strain by the same method as that described above.

The obtained KNK005dZ/dbktB/dA1528 strain is a strain, in which the region from the start codon to the stop codon of each of the phaZ1 gene and the phaZ6 gene on the chromosome of the *Cupriavidus necator* H16 strain was deleted, the region from the 16th codon to the stop codon of the phaZ2 gene was further deleted, a gene encoding PHA synthase having the amino acid sequence as shown in SEQ ID NO: 2 was introduced onto the chromosome, the region from the start codon to the stop codon of the bktB structural gene was deleted, and the region from the start codon to the stop codon of the A1528 structural gene was further deleted.

(Production Example 5) Production of KNK005dZ/Trc-J4b/dphaA Strain

Using the plasmid vector for gene disruption pNS2X-sacB+phaAUD produced in Production Example 1, and also using the KNK005dZ/trc-J4b strain as a parent strain, a KNK005dZ/trc-J4b/dphaA strain was produced as a gene-disrupted strain by the same method as that described above.

The obtained KNK005dZ/trc-J4b/dphaA strain is a strain, in which the region from the start codon to the stop codon of each of the phaZ1 gene and the phaZ6 gene on the chromosome of the *Cupriavidus necator* H16 strain was deleted, the region from the 16th codon to the stop codon of the phaZ2 gene was further deleted, a gene encoding PHA synthase having the amino acid sequence as shown in SEQ ID NO: 2 was introduced onto the chromosome, the expression of the (R)-specific enoyl-CoA hydratase gene on the chromosome was enhanced, and the region from the start codon to the stop codon of the phaA structural gene was further deleted.

(Production Example 6) Production of KNK005dZ/trc-J4b/dbktB Strain

Using the plasmid vector for gene disruption pNS2X-sacB+bktBUD produced in Production Example 2, and also using the KNK005dZ/trc-J4b strain as a parent strain, a KNK005dZ/trc-J4b/dbktB strain was produced as a gene-disrupted strain by the same method as that described above.

The obtained KNK005dZ/trc-J4b/dbktB strain is a strain, in which the region from the start codon to the stop codon of each of the phaZ1 gene and the phaZ6 gene on the chromosome of the *Cupriavidus necator* H16 strain was deleted, the region from the 16th codon to the stop codon of the phaZ2 gene was further deleted, a gene encoding PHA synthase having the amino acid sequence as shown in SEQ ID NO: 2 was introduced onto the chromosome, the expression of the (R)-specific enoyl-CoA hydratase gene on the chromosome was enhanced, and the region from the start codon to the stop codon of the bktB structural gene was further deleted.

(Production Example 7) Production of KNK005dZ/Trc-J4b/dA1528 Strain

Using the plasmid vector for gene disruption pNS2X-sacB+A1528UD produced in Production Example 3, and also using the KNK005dZ/trc-J4b strain as a parent strain, a KNK005dZ/trc-J4b/dA1528 strain was produced as a gene-disrupted strain by the same method as that described above.

The obtained KNK005dZ/trc-J4b/dA1528 strain is a strain, in which the region from the start codon to the stop codon of each of the phaZ1 gene and the phaZ6 gene on the chromosome of the *Cupriavidus necator* H16 strain was deleted, the region from the 16th codon to the stop codon of the phaZ2 gene was further deleted, a gene encoding PHA synthase having the amino acid sequence as shown in SEQ ID NO: 2 was introduced onto the chromosome, the expression of the (R)-specific enoyl-CoA hydratase gene on the chromosome was enhanced, and the region from the start codon to the stop codon of the A1528 structural gene was further deleted.

(Production Example 8) Production of KNK005dZ/Trc-J4b/dbktB/dA1528 Strain

Using the plasmid vector for gene disruption pNS2X-sacB+A1528UD produced in Production Example 3, and also using the KNK005dZ/trc-J4b/dbktB strain produced in Production Example 6 as a parent strain, a KNK005dZ/trc-J4b/dbktB/dA1528 strain was produced as a gene-disrupted strain by the same method as that described above.

The obtained KNK005dZ/trc-J4b/dbktB/dA1528 strain is a strain, in which the region from the start codon to the stop codon of each of the phaZ1 gene and the phaZ6 gene on the chromosome of the *Cupriavidus necator* H16 strain was deleted, the region from the 16th codon to the stop codon of the phaZ2 gene was further deleted, a gene encoding PHA synthase having the amino acid sequence as shown in SEQ ID NO: 2 was introduced onto the chromosome, the expression of the (R)-specific enoyl-CoA hydratase gene on the chromosome was enhanced, the region from the start codon to the stop codon of the bktB structural gene was deleted, and the region from the start codon to the stop codon of the A1528 structural gene was further deleted.

(Production Example 9) Production of KNK005dZ/Trc-J4b/lacN17-NSDG Strain

At the onset, a plasmid for gene disruption was produced. The production was carried out as follows.

According to PCR using synthetic oligo DNA, a DNA fragment (SEQ ID NO: 15) comprising nucleotide sequences upstream and downstream of a phaZ6 structural gene, a lacN17 promoter having the nucleotide sequence as shown in SEQ ID NO: 11, and a gene encoding PHA synthase having the amino acid sequence as shown in SEQ ID NO: 2, was obtained. The obtained DNA fragment was digested with the restriction enzyme SwaI. This DNA fragment was ligated with the vector pNS2X-sacB described in Japanese Patent Publication (Kokai) No. 2007-259708 A, which had also been digested with SwaI, using DNA ligase (Ligation High (manufactured by Toyobo Co., Ltd.)), so as to produce the plasmid vector for gene insertion pNS2X-sacB+lacN17-NSDG.

Subsequently, using the plasmid for gene insertion vector pNS2X-sacB+lacN17-NSDG, and also using the KNK005dZ/trc-J4b strain as a parent strain, chromosomal DNA was modified by the same method as the above-described gene disruption, so as to produce a KNK005dZ/trc-J4b/lacN17-NSDG strain as a gene-inserted strain.

The obtained KNK005dZ/trc-J4b/lacN17-NSDG strain is a strain, in which the region from the start codon to the stop codon of each of the phaZ1 gene and the phaZ6 gene on the chromosome of the *Cupriavidus necator* H16 strain was deleted, the region from the 16th codon to the stop codon of the phaZ2 gene was further deleted, two copies of genes encoding PHA synthase having the amino acid sequence as shown in SEQ ID NO: 2 were introduced onto the chromosome, and the expression of the (R)-specific enoyl-CoA hydratase gene on the chromosome was further enhanced.

(Production Example 10) Production of KNK005dZ/Trc-J4b/lacN17-NSDG/dA0462 Strain At the onset, a plasmid for gene disruption was produced. The production was carried out as follows.

According to PCR using synthetic oligo DNA, a DNA fragment (SEQ ID NO: 16) comprising nucleotide sequences upstream and downstream of an A0462 structural gene was obtained. The obtained DNA fragment was digested with the restriction enzyme SwaI. This DNA fragment was ligated with the vector pNS2X-sacB described in Japanese Patent Publication (Kokai) No. 2007-259708 A, which had also been digested with SwaI, using DNA ligase (Ligation High (manufactured by Toyobo Co., Ltd.)), so as to produce the plasmid vector for gene disruption pNS2X-sacB+A0462UD comprising the nucleotide sequences upstream and downstream of the A0462 structural gene.

Subsequently, using the plasmid for gene disruption vector pNS2X-sacB+A0462UD, and also using the KNK005dZ/trc-J4b/lacN17-NSDG strain produced in Production Example 9 as a parent strain, a KNK005dZ/trc-J4b/lacN17-NSDG/dA0462 strain was produced as a gene-disrupted strain by the same method as that described above.

The obtained KNK005dZ/trc-J4b/lacN17-NSDG/dA0462 strain is a strain, in which the region from the start codon to the stop codon of each of the phaZ1 gene and the phaZ6 gene on the chromosome of the *Cupriavidus necator* H16 strain was deleted, the region from the 16th codon to the stop codon of the phaZ2 gene was further deleted, two copies of genes encoding PHA synthase having the amino acid sequence as shown in SEQ ID NO: 2 were introduced onto the chromosome, the expression of the (R)-specific enoyl-CoA hydratase gene on the chromosome was enhanced, and the region from the start codon to the stop codon of the A0462 structural gene was further deleted.

(Production Example 11) Production of KNK005dZ/Trc-J4b/lacN17-NSDG/dbktB Strain

Using the plasmid vector for gene disruption pNS2X-sacB+bktBUD produced in Production Example 2, and also using the KNK005dZ/trc-J4b/lacN17-NSDG strain produced in Production Example 9 as a parent strain, a KNK005dZ/trc-J4b/lacN17-NSDG/dbktB strain was produced as a gene-disrupted strain.

The obtained KNK005dZ/trc-J4b/lacN17-NSDG/dbktB strain is a strain, in which the region from the start codon to the stop codon of each of the phaZ,1 gene and the phaZ6 gene on the chromosome of the *Cupriavidus necator* H16 strain was deleted, the region from the 16th codon to the stop codon of the phaZ2 gene was further deleted, two copies of genes encoding PHA synthase having the amino acid sequence as shown in SEQ ID NO: 2 were introduced onto the chromosome, the expression of the (R)-specific enoyl-CoA hydratase gene on the chromosome was enhanced, and the region from the start codon to the stop codon of the bktB structural gene was further deleted.

(Production Example 12) Production of KNK005dZ/Trc-J4b/lacN17-NSDG/dA1528 Strain Using the plasmid vector for gene disruption pNS2X-sacB+A1528UD produced in Production Example 3, and also using the KNK005dZ/trc-J4b/lacN17-NSDG strain produced in Production Example 9 as a parent strain, a KNK005dZ/trc-J4b/lacN17-NSDG/dA1528 strain was produced as a gene-disrupted strain by the same method as that described above.

The obtained KNK005dZ/trc-J4b/lacN17-NSDG/dA1528 strain is a strain, in which the region from the start codon to the stop codon of each of the phaZ1 gene and the phaZ6 gene on the chromosome of the *Cupriavidus necator* H16 strain was deleted, the region from the 16th codon to the stop codon of the phaZ2 gene was further deleted, two copies of genes encoding PHA synthase having the amino acid sequence as shown in SEQ ID NO: 2 were introduced onto the chromosome, the expression of the (R)-specific enoyl-CoA hydratase gene on the chromosome was enhanced, and the region from the start codon to the stop codon of the A1528 structural gene was further deleted.

(Production Example 13) Production of KNK005dZ/trc-J4b/lacN17−NSDG/dbktB/dA1528 Strain Using the plasmid vector for gene disruption pNS2X-sacB+A1528UD produced in Production Example 3, and also using the KNK005dZ/trc-J4b/lacN17−NSDG/dbktB strain produced in Production Example 11 as a parent strain, a KNK005dZ/trc-J4b/lacN17−NSDG/dbktB/dA1528 strain was produced as a gene-disrupted strain by the same method as that described above.

The obtained KNK005dZ/trc-J4b/lacN17−NSDG/dbktB/dA1528 strain is a strain, in which the region from the start codon to the stop codon of each of the phaZ1 gene and the phaZ6 gene on the chromosome of the *Cupriavidus necator* H16 strain was deleted, the region from the 16th codon to the stop codon of the phaZ2 gene was further deleted, two copies of genes encoding PHA synthase having the amino acid sequence as shown in SEQ ID NO: 2 were introduced onto the chromosome, the expression of the (R)-specific enoyl-CoA hydratase gene on the chromosome was enhanced, the region from the start codon to the stop codon of the bktB structural gene was deleted, and the region from the start codon to the stop codon of the A1528 structural gene was further deleted.

(Comparative Example 1) Production of PHA by KNK005dZ Strain

The composition of a seed culture medium was 1 w/v % Meat-extract, 1 w/v % Bacto-Trypton, 0.2 w/v % Yeast-extract, 0.9 w/v % $Na_2HPO_4 \cdot 12H_2O$, and 0.15 w/v % $KH_2PO_4$.

The composition of a production medium used in the production of PHA was 1.1 w/v % $Na_2HPO_4 \cdot 12H_2O$, 0.19 w/v % $KH_2PO_4$, 0.13 w/v % $(NH_4)_2SO_4$, 0.1 w/v % $MgSO_4 \cdot 7H_2O$, and 0.1 v/v % trace metal salt solution (prepared by dissolving 1.6 w/v % $FeCl_3 \cdot 6H_2O$, 1 w/v % $CaCl_2 \cdot 2H_2O$, 0.02 w/v % $CoCl_2 \cdot 6H_2O$, 0.016 w/v % $CuSO_4 \cdot 5H_2O$, and 0.012 w/v % $NiCl_2 \cdot 6H_2O$ in 0.1N hydrochloric acid). As a carbon source, palm kernel oil was added to the medium to a concentration of 1.5 w/v %.

A glycerol stock (50 μL) of the KNK005dZ strain was seeded on a seed culture medium (5 mL) and was then subjected to shaking culture at a culture temperature of 30° C. for 24 hours. The obtained culture broth was used as the seed culture.

As a culture for producing PHA, the above-described seed culture (1.0 v/v %) was seeded in a Sakaguchi flask in which 50 mL of the production medium had been placed, and it was then subjected to a shaking culture at a culture temperature of 30° C. After completion of the culture for 72 hours, the cells were recovered by centrifugation, washed with methanol, and then freeze-dried. Thereafter, the dry weight of the cells was measured.

The amount of the produced PHA and the copolymer composition ratio were calculated as follows. That is, 1 ml of a sulfuric acid-methanol mixture (15:85) and 1 ml of chloroform were added to approximately 20 mg of the obtained dry cells, followed by closely sealing and heating at 100° C. for 140 minutes to obtain a methyl ester which is a PHA decomposition product. After cooling, 0.5 ml of deionized water was added to the product and then well mixed. Thereafter, the mixture was left to stand until the water layer was separated from the organic layer. After that, the composition of monomer units in the PHA decomposition product contained in the fractionated organic layer was analyzed by capillary gas chromatography. As a gas chromatograph, GC-17A manufactured by Shimadzu Corporation was used. As a capillary column, NEUTRA BOND-1 manufactured by GL Sciences (column length: 25 m, column inner diameter: 0.25 mm, and liquid film thickness: 0.4 μm) was used. As a carrier gas, He was used, the column import pressure was set at 100 kPa, and 1 μl of sample was injected into the column. With regard to temperature conditions, the temperature was increased at a rate of 8° C./min up to an initial temperature of 50° C. to 200° C., and further, the temperature was increased at a rate of 30° C./min up to a temperature of 200° C. to 290° C. The analysis was carried out under the above-described conditions, and as a result, the PHA production amount and the 3HH composition ratio are indicated in Table 1.

TABLE 1

| Strain Name | | PHA Production amount (g/L) | 3HH composition ratio (mol %) |
|---|---|---|---|
| Comparative Example 1 | KNK005dZ | 16.4 | 3.0 |
| Comparative Example 2 | KNK005dZ/dphaA | 8.0 | 2.9 |
| Example 1 | KNK005dZ/dbktB | 14.9 | 6.5 |
| Example 2 | KNK005dZ/dA1528 | 15.2 | 3.3 |
| Example 3 | KNK005dZ/dbktB/dA1528 | 14.2 | 14.3 |
| Comparative Example 3 | KNK005dZ/trc-J4b | 14.5 | 10.1 |
| Comparative Example 4 | KNK005dZ/trc-J4b/dphaA | 8.2 | 10.1 |
| Example 4 | KNK005dZ/trc-J4b/dbktB | 14.6 | 14.3 |
| Example 5 | KNK005dZ/trc-J4b/dA1528 | 13.7 | 10.8 |
| Example 6 | KNK005dZ/trc-J4b/dbktB/dA1528 | 12.8 | 23.0 |
| Comparative Example 5 | KNK005dZ/trc-J4b/lacN17-NSDG | 14.9 | 12.9 |
| Comparative Example 6 | KNK005dZ/trc-J4b/lacN17-NSDG/dA0462 | 11.8 | 12.4 |
| Example 7 | KNK005dZ/trc-J4b/lacN17-NSDG/dbktB | 14.4 | 17.1 |
| Example 8 | KNK005dZ/trc-J4b/lacN17-NSDG/dA1528 | 13.5 | 13.6 |
| Example 9 | KNK005dZ/trc-J4b/lacN17-NSDG/dbktB/dA1528 | 6.2 | 29.5 |

The PHA produced in the present comparative example was P(3HB-co-3HH) comprising 3HH monomer unit at 3.0 mol %.

(Comparative Example 2) Production of PHA by KNK005dZ/dphaA Strain

The composition of the seed culture medium, the composition of a PHA production medium, and a carbon source were the same as those described in Comparative Example 1.

The KNK005dZ/dphaA strain produced in Production Example 1 was cultured by the same method as that of Comparative Example 1, and the PHA production amount and the 3HH composition ratio were calculated by the same method as that of Comparative Example 1. The determined PHA production amount and 3HH composition ratio are indicated in Table 1.

The PHA produced in the present comparative example was P(3HB-co-3HH) having a 3HH composition ratio of 2.9 mol %. Thus, the composition ratio of 3HH in the produced PHA copolymer was not improved by disruption of the phaA gene, and the 3HH composition ratio-increasing rate was 1 or less.

(Example 1) Production of PHA by KNK005dZ/dbktB Strain

The composition of a seed culture medium, the composition of a PHA production medium, and a carbon source were the same as those described in Comparative Example 1.

The KNK005dZ/dbktB strain produced in Production Example 2 was cultured by the same method as that of Comparative Example 1, and the PHA production amount and the 3HH composition ratio were calculated by the same method as that of Comparative Example 1. The determined PHA production amount and 3HH composition ratio are indicated in Table 1.

The PHA produced in the present example was P(3HB-co-3HH) having a 3HH composition ratio of 6.5 mol %. Thus, the composition ratio of 3HH in the produced PHA copolymer was improved by disruption of the bktB gene. The aforementioned product (produced PHA amount-reducing rate×3HH composition ratio-increasing rate) was 1.97.

(Example 2) Production of PHA by KNK005dZ/dA1528 Strain

The composition of a seed culture medium, the composition of a PHA production medium, and a carbon source were the same as those described in Comparative Example 1.

The KNK005dZ/dA1528 strain produced in Production Example 3 was cultured by the same method as that of Comparative Example 1, and the PHA production amount and the 3HH composition ratio were calculated by the same method as that of Comparative Example 1. The determined PHA production amount and 3HH composition ratio are indicated in Table 1.

The PHA produced in the present example was P(3HB-co-3HH) having a 3HH composition ratio of 3.3 mol %. Thus, the composition ratio of 3HH in the produced PHA copolymer was improved by disruption of the A1528 gene. The aforementioned product (produced PHA amount-reducing rate×3HH composition ratio-increasing rate) was 1.02.

(Example 3) Production of PHA by KNK005dZ/dbktB/dA1528 Strain

The composition of a seed culture medium, the composition of a PHA production medium, and a carbon source were the same as those described in Comparative Example 1.

The KNK005dZ/dbktB/dA1528 strain produced in Production Example 4 was cultured by the same method as that of Comparative Example 1, and the amount of PHA produced and the 3HH composition ratio were calculated by the same method as that of Comparative Example 1. The determined PHA production amount and 3HH composition ratio are indicated in Table 1.

The PHA produced in the present example was P(3HB-co-3HH) having a 3HH composition ratio of 14.3 mol %. Thus, the composition ratio of 3HH in the produced PHA copolymer was significantly improved by disruption of the bktB gene and the A1528 gene. The aforementioned product (produced PHA amount-reducing rate×3HH composition ratio-increasing rate) was 4.13.

(Comparative Example 3) Production of PHA by KNK005dZ/Trc-J4b Strain

The composition of a seed culture medium, the composition of a PHA production medium, and a carbon source were the same as those described in Comparative Example 1.

The KNK005dZ/trc-J4b strain was cultured by the same method as that of Comparative Example 1, and the PHA production amount and the 3HH composition ratio were calculated by the same method as that of Comparative Example 1. The determined PHA production amount and 3HH composition ratio are indicated in Table 1.

The PHA produced in the present comparative example was P(3HB-co-3HH) having a 3HH composition ratio of 10.1 mol %.

(Comparative Example 4) Production of PHA by KNK005dZ/Trc-J4b/dphaA Strain

The composition of a seed culture medium, the composition of a PHA production medium, and a carbon source were the same as those described in Comparative Example 1.

The KNK005dZ/trc-J4b/dphaA strain produced in Production Example 5 was cultured by the same method as that of Comparative Example 1, and the amount of PHA produced and the 3HH composition ratio were calculated by the same method as that of Comparative Example 1. The determined PHA production amount and 3HH composition ratio are indicated in Table 1.

The PHA produced in the present example was P(3HB-co-3HH) having a 3HH composition ratio of 10.1 mol %. Thus, the composition ratio of 3HH in the produced PHA copolymer was not improved by disruption of the phaA gene, and the 3HH composition ratio-increasing rate was 1 or less.

(Example 4) Production of PHA by KNK005dZ/Trc-J4b/dbktB Strain

The composition of a seed culture medium, the composition of a PHA production medium, and a carbon source were the same as those described in Comparative Example 1.

The KNK005dZ/trc-J4b/dbktB strain produced in Production Example 6 was cultured by the same method as that of Comparative Example 1, and the PHA production amount and the 3HH composition ratio were calculated by the same method as that of Comparative Example 1. The determined PHA production amount and 3HH composition ratio are indicated in Table 1.

The PHA produced in the present example was P(3HB-co-3HH) having a 3HH composition ratio of 14.3 mol %. Specifically, the composition ratio of 3HH in the produced PHA copolymer was improved by disruption of the bktB gene. The aforementioned product (produced PHA amount-reducing rate×3HH composition ratio-increasing rate) was 1.43.

(Example 5) Production of PHA by KNK005dZ/Trc-J4b/dA1528 Strain

The composition of a seed culture medium, the composition of a PHA production medium, and a carbon source were the same as those described in Comparative Example 1.

The KNK005dZ/trc-J4b/dA1528 strain produced in Production Example 7 was cultured by the same method as that of Comparative Example 1, and the amount of PHA produced and the 3HH composition ratio were calculated by the same method as that of Comparative Example 1. The determined PHA production amount and 3HH composition ratio are indicated in Table 1.

The PHA produced in the present example was P(3HB-co-3HH) having a 3HH composition ratio of 10.8 mol %. Thus, the composition ratio of 3HH in the produced PHA copolymer was improved by disruption of the A1528 gene. The aforementioned product (produced PHA amount-reducing rate×3HH composition ratio-increasing rate) was 1.01.

(Example 6) Production of PHA by KNK005dZ/trc-J4b/dbktB/dA1528 Strain

The composition of a seed culture medium, the composition of a PHA production medium, and a carbon source were the same as those described in Comparative Example 1.

The KNK005dZ/trc-J4b/dbktB/dA1528 strain produced in Production Example 8 was cultured by the same method as that of Comparative Example 1, and the amount of PHA produced and the 3HH composition ratio were calculated by the same method as that of Comparative Example 1. The determined PHA production amount and 3HH composition ratio are indicated in Table 1.

The PHA produced in the present example was P(3HB-co-3HH) having a 3HH composition ratio of 23.0 mol %. Specifically, the composition ratio of 3HH in the produced PHA copolymer was significantly improved by disruption of the bktB gene and the A1528 gene. The aforementioned product (produced PHA amount-reducing rate×3HH composition ratio-increasing rate) was 2.01.

(Comparative Example 5) Production of PHA by KNK005dZ/trc-J4b/lacN17–NSDG Strain The composition of a seed culture medium, the composition of a PHA production medium, and a carbon source were the same as those described in Comparative Example 1.

The KNK005dZ/trc-J4b/lacN17–NSDG strain produced in Production Example 9 was cultured by the same method as that of Comparative Example 1, and the amount of PHA produced and the 3HH composition ratio were calculated by the same method as that of Comparative Example 1. The determined PHA production amount and 3HH composition ratio are indicated in Table 1.

The PHA produced in the present comparative example was P(3HB-co-3HH) having a 3HH composition ratio of 12.9 mol %.

(Comparative Example 6) Production of PHA by KNK005dZ/trc-J4b/lacN17–NSDG/dA0462 Strain The composition of a seed culture medium, the composition of a PHA production medium, and a carbon source were the same as those described in Comparative Example 1.

The KNK005dZ/trc-J4b/lacN17–NSDG/dA0462 strain produced in Production Example 10 was cultured by the same method as that of Comparative Example 1, and the amount of PHA produced and the 3HH composition ratio were calculated by the same method as that of Comparative Example 1. The determined PHA production amount and 3HH composition ratio are indicated in Table 1.

The PHA produced in the present comparative example was P(3HB-co-3HH) having a 3HH composition ratio of 12.4 mol %. Thus, the composition ratio of 3HH in the produced PHA copolymer was not improved by disruption of the A0462 gene, and the 3HH composition ratio-increasing rate was 1 or less.

(Example 7) Production of PHA by KNK005dZ/Trc-J4b/lacN17–NSDG/dbktB Strain

The composition of a seed culture medium, the composition of a PHA production medium, and a carbon source were the same as those described in Comparative Example 1.

The KNK005dZ/trc-J4b/lacN17–NSDG/dbktB strain produced in Production Example 11 was cultured by the same method as that of Comparative Example 1, and the amount of PHA produced and the 3HH composition ratio were calculated by the same method as that of Comparative Example 1. The determined PHA production amount and 3HH composition ratio are indicated in Table 1.

The PHA produced in the present example was P(3HB-co-3HH) having a 3HH composition ratio of 17.1 mol %. Thus, the composition ratio of 3HH in the produced PHA copolymer was improved by disruption of the bktB gene. The aforementioned product (produced PHA amount-reducing rate×3HH composition ratio-increasing rate) was 1.28.

(Example 8) Production of PHA by KNK005dZ/Trc-J4b/lacN17–NSDG/dA1528 Strain

The composition of a seed culture medium, the composition of a PHA production medium, and a carbon source were the same as those described in Comparative Example 1.

The KNK005dZ/trc-J4b/lacN17–NSDG/dA1528 strain produced in Production Example 12 was cultured by the same method as that of Comparative Example 1, and the amount of PHA produced and the 3HH composition ratio were calculated by the same method as that of Comparative Example 1. The determined PHA production amount and 3HH composition ratio are indicated in Table 1.

The PHA produced in the present example was P(3HB-co-3HH) having a 3HH composition ratio of 13.6 mol %. Thus, the composition ratio of 3HH in the produced PHA copolymer was improved by disruption of the A1528 gene. The aforementioned product (produced PHA amount-reducing rate×3HH composition ratio-increasing rate) was 0.96.

(Example 9) Production of PHA by KNK005dZ/trc-J4b/lacN17–NSDG/dbktB/dA1528 Strain The composition of a seed culture medium, the composition of a PHA production medium, and a carbon source were the same as those described in Comparative Example 1.

The KNK005dZ/trc-J4b/lacN17-NSDG/dbktB/dA1528 strain produced in Production Example 13 was cultured by the same method as that of Comparative Example 1, and the amount of PHA produced and the 3HH composition ratio were calculated by the same method as that of Comparative Example 1. The determined PHA production amount and 3HH composition ratio are indicated in Table 1.

The PHA produced in the present example was P(3HB-co-3HH) having a 3HH composition ratio of 29.5 mol %. Thus, the composition ratio of 3HH in the produced PHA copolymer was significantly improved by disruption of the bktB gene and the A1528 gene. The aforementioned product (produced PHA amount-reducing rate×3HH composition ratio-increasing rate) was 0.95.

INDUSTRIAL APPLICABILITY

According to the present invention, it is possible to synthesize a PHA copolymer comprising 3HH at a high composition ratio of, for example, 14 mol % or higher, or 20 mol % or higher, without significantly reducing the amount of PHA produced, and the thus produced PHA can be used in intended applications that require polymers with high flexibility.

Sequence Listing Free Text

SEQ ID NO: 11: *Escherichia coli*-derived artificially modified promoter

All publications, patents and patent applications cited herein are incorporated by reference herein in their entirety.

---

The invention claimed is:

1. A transformed microorganism that is a bacterium belonging to the genus *Cupriavidus*, comprising:
   a PHA synthase gene capable of synthesizing a polyhydroxyalkanoate (PHA) copolymer comprising 3-hydroxyhexanoate (3HH) monomer unit and 3-hydroxybutanoate (3HB) monomer unit; and
   a gene encoding a protein having (R)-specific enoyl-CoA hydratase activity,
   wherein in the transformed microorganism, at least two genes encoding a β-ketothiolase enzyme are disrupted such that the activity of the β-ketothiolase enzyme having thiolysis activity for β-ketohexanoyl-CoA is reduced or lost as compared to a corresponding non-transformed microorganism, resulting in increase in a 3HH ratio in a PHA copolymer produced in the transformed microorganism compared to that in a non-transformed microorganism,
   wherein a phaA gene is not disrupted in the transformed microorganism, and
   wherein the at least two genes encoding the β-ketothiolase enzyme is a combination of the gene (i) and gene (ii):
   (i) a bktB gene comprising the nucleotide sequence of SEQ ID NO: 7, or a nucleotide sequence having 85% or higher sequence identity to the nucleotide sequence of SEQ ID NO: 7; and
   (ii) an A1528 gene having comprising the nucleotide sequence of SEQ ID NO: 8, or a nucleotide sequence having 85% or higher sequence identity to the nucleotide sequence of SEQ ID NO: 8.

2. The transformed microorganism according to claim 1, wherein in the transformed microorganism, expression of the gene encoding a protein having (R)-specific enoyl-CoA hydratase activity is enhanced as compared to a corresponding non-transformed microorganism.

3. The transformed microorganism according to claim 1, wherein expression of the PHA synthase gene is enhanced as compared to a corresponding non-transformed microorganism.

4. The transformed microorganism according to claim 1, wherein the bacterium belonging to the genus *Cupriavidus* is *Cupriavidus necator*.

5. The transformed microorganism according to claim 4, wherein the *Cupriavidus necator* is *Cupriavidus necator* H16 strain.

6. A method for producing a PHA copolymer comprising 3HH monomer unit and 3HB monomer unit, the method comprising:
   culturing the transformed microorganism of claim 1 using a carbon source comprising an oil or a fat or a fatty acid; and
   recovering a PHA copolymer comprising 3HH monomer unit and 3HB monomer unit.

7. The method according to claim 6, wherein the PHA copolymer is poly(3-hydroxybutyrate-co-3-hydroxyhexanoate) (P(3HB-co-3HH)).

8. The transformed microorganism according to claim 1, wherein in the transformed microorganism, the at least two genes encoding the at last one β-ketothiolase enzyme having thiolysis activity for β-ketohexanoyl-CoA is disrupted such that the thiolysis activity of the β-ketothiolase enzyme is lost.

9. The transformed microorganism according to claim 1, wherein in the transformed microorganism, the at least two genes encoding the at last one β-ketothiolase enzyme having thiolysis activity for β-ketohexanoyl-CoA is disrupted such that the thiolysis activity of the β-ketothiolase enzyme is reduced as compared to a corresponding non-transformed microorganism.

10. The transformed microorganism according to claim 1, wherein the bktB gene comprises a nucleotide sequence having at least 95% sequence identity to the nucleotide sequence of SEQ ID NO: 7.

11. The transformed microorganism according to claim 1, wherein the A1528 gene comprises a nucleotide sequence having at least 95% sequence identity to the nucleotide sequence of SEQ ID NO: 8.

12. The transformed microorganism according to claim 1, wherein the reduction of the activity of the β-ketothiolase enzyme in the microorganism is caused by genome editing technique, CRISPR/Cas system, homologous recombination technique, transposon technique, modification of a promoter region for the gene, modification of a ribosome binding sequence for the gene, or a combination thereof.

13. The transformed microorganism according to claim 1, wherein a value of produced PHA amount-reducing rate×3HH composition ratio-increasing rate is at least 0.95.

* * * * *

SEQUENCE LISTING

<160> NUMBER OF SEQ ID NOS: 16

<210> SEQ ID NO 1
<211> LENGTH: 594
<212> TYPE: PRT
<213> ORGANISM: Aeromonas caviae

<400> SEQUENCE: 1

```
Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
            20                  25                  30

Gln Ala Leu Leu Gln Thr Asn Leu Asp Asp Leu Gly Gln Val Leu Glu
        35                  40                  45

Gln Gly Ser Gln Gln Pro Trp Gln Leu Ile Gln Ala Gln Met Asn Trp
    50                  55                  60

Trp Gln Asp Gln Leu Lys Leu Met Gln His Thr Leu Leu Lys Ser Ala
65                  70                  75                  80

Gly Gln Pro Ser Glu Pro Val Ile Thr Pro Glu Arg Ser Asp Arg Arg
                85                  90                  95

Phe Lys Ala Glu Ala Trp Ser Glu Gln Pro Ile Tyr Asp Tyr Leu Lys
            100                 105                 110

Gln Ser Tyr Leu Leu Thr Ala Arg His Leu Leu Ala Ser Val Asp Ala
        115                 120                 125

Leu Glu Gly Val Pro Gln Lys Ser Arg Glu Arg Leu Arg Phe Phe Thr
    130                 135                 140

Arg Gln Tyr Val Asn Ala Met Ala Pro Ser Asn Phe Leu Ala Thr Asn
145                 150                 155                 160

Pro Glu Leu Leu Lys Leu Thr Leu Glu Ser Asp Gly Gln Asn Leu Val
                165                 170                 175

Arg Gly Leu Ala Leu Leu Ala Glu Asp Leu Glu Arg Ser Ala Asp Gln
            180                 185                 190

Leu Asn Ile Arg Leu Thr Asp Glu Ser Ala Phe Glu Leu Gly Arg Asp
        195                 200                 205

Leu Ala Leu Thr Pro Gly Arg Val Val Gln Arg Thr Glu Leu Tyr Glu
    210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg
                245                 250                 255

Pro Gln Asn Ser Leu Val Ala Trp Leu Val Ala Gln Gly Gln Thr Val
            260                 265                 270
```

```
Phe Met Ile Ser Trp Arg Asn Pro Gly Val Ala Gln Ala Gln Ile Asp
            275                 280                 285

Leu Asp Asp Tyr Val Val Asp Gly Val Ile Ala Ala Leu Asp Gly Val
        290                 295                 300

Glu Ala Ala Thr Gly Glu Arg Glu Val His Gly Ile Gly Tyr Cys Ile
305                 310                 315                 320

Gly Gly Thr Ala Leu Ser Leu Ala Met Gly Trp Leu Ala Ala Arg Arg
                325                 330                 335

Gln Lys Gln Arg Val Arg Thr Ala Leu Phe Thr Thr Leu Leu Asp
            340                 345                 350

Phe Ser Gln Pro Gly Glu Leu Gly Ile Phe Ile His Glu Pro Ile Ile
        355                 360                 365

Ala Ala Leu Glu Ala Gln Asn Glu Ala Lys Gly Ile Met Asp Gly Arg
    370                 375                 380

Gln Leu Ala Val Ser Phe Ser Leu Leu Arg Glu Asn Ser Leu Tyr Trp
385                 390                 395                 400

Asn Tyr Tyr Ile Asp Ser Tyr Leu Lys Gly Gln Ser Pro Val Ala Phe
                405                 410                 415

Asp Leu Leu His Trp Asn Ser Asp Ser Thr Asn Val Ala Gly Lys Thr
            420                 425                 430

His Asn Ser Leu Leu Arg Arg Leu Tyr Leu Glu Asn Gln Leu Val Lys
        435                 440                 445

Gly Glu Leu Lys Ile Arg Asn Thr Arg Ile Asp Leu Gly Lys Val Lys
    450                 455                 460

Thr Pro Val Leu Leu Val Ser Ala Val Asp Asp His Ile Ala Leu Trp
465                 470                 475                 480

Gln Gly Thr Trp Gln Gly Met Lys Leu Phe Gly Gly Glu Gln Arg Phe
                485                 490                 495

Leu Leu Ala Glu Ser Gly His Ile Ala Gly Ile Ile Asn Pro Pro Ala
            500                 505                 510

Ala Asn Lys Tyr Gly Phe Trp His Asn Gly Ala Glu Ala Glu Ser Pro
        515                 520                 525

Glu Ser Trp Leu Ala Gly Ala Thr His Gln Gly Gly Ser Trp Trp Pro
    530                 535                 540

Glu Met Met Gly Phe Ile Gln Asn Arg Asp Glu Gly Ser Glu Pro Val
545                 550                 555                 560

Pro Ala Arg Val Pro Glu Glu Gly Leu Ala Pro Gly His Tyr
                565                 570                 575

Val Lys Val Arg Leu Asn Pro Val Phe Ala Cys Pro Thr Glu Glu Asp
            580                 585                 590

Ala Ala

<210> SEQ ID NO 2
<211> LENGTH: 594
<212> TYPE: PRT
<213> ORGANISM: Aeromonas caviae

<400> SEQUENCE: 2

Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
            20                  25                  30

Gln Ala Leu Leu Gln Thr Asn Leu Asp Asp Leu Gly Gln Val Leu Glu
        35                  40                  45
```

```
Gln Gly Ser Gln Gln Pro Trp Gln Leu Ile Gln Ala Gln Met Asn Trp
    50                  55                  60
Trp Gln Asp Gln Leu Lys Leu Met Gln His Thr Leu Leu Lys Ser Ala
65                  70                  75                  80
Gly Gln Pro Ser Glu Pro Val Ile Thr Pro Glu Arg Ser Asp Arg Arg
                85                  90                  95
Phe Lys Ala Glu Ala Trp Ser Glu Gln Pro Ile Tyr Asp Tyr Leu Lys
            100                 105                 110
Gln Ser Tyr Leu Leu Thr Ala Arg His Leu Leu Ala Ser Val Asp Ala
        115                 120                 125
Leu Glu Gly Val Pro Gln Lys Ser Arg Glu Arg Leu Arg Phe Phe Thr
    130                 135                 140
Arg Gln Tyr Val Ser Ala Met Ala Pro Ser Asn Phe Leu Ala Thr Asn
145                 150                 155                 160
Pro Glu Leu Leu Lys Leu Thr Leu Glu Ser Gly Gly Gln Asn Leu Val
                165                 170                 175
Arg Gly Leu Ala Leu Leu Ala Glu Asp Leu Glu Arg Ser Ala Asp Gln
            180                 185                 190
Leu Asn Ile Arg Leu Thr Asp Glu Ser Ala Phe Glu Leu Gly Arg Asp
        195                 200                 205
Leu Ala Leu Thr Pro Gly Arg Val Val Gln Arg Thr Glu Leu Tyr Glu
    210                 215                 220
Leu Ile Gln Tyr Ser Pro Thr Thr Glu Thr Val Gly Lys Thr Pro Val
225                 230                 235                 240
Leu Ile Val Pro Pro Phe Ile Asn Lys Tyr Tyr Ile Met Asp Met Arg
                245                 250                 255
Pro Gln Asn Ser Leu Val Ala Trp Leu Val Ala Gln Gly Gln Thr Val
            260                 265                 270
Phe Met Ile Ser Trp Arg Asn Pro Gly Val Ala Gln Ala Gln Ile Asp
        275                 280                 285
Leu Asp Asp Tyr Val Val Asp Gly Val Ile Ala Ala Leu Asp Gly Val
    290                 295                 300
Glu Ala Ala Thr Gly Glu Arg Glu Val His Gly Ile Gly Tyr Cys Ile
305                 310                 315                 320
Gly Gly Thr Ala Leu Ser Leu Ala Met Gly Trp Leu Ala Ala Arg Arg
                325                 330                 335
Gln Lys Gln Arg Val Arg Thr Ala Thr Leu Phe Thr Thr Leu Leu Asp
            340                 345                 350
Phe Ser Gln Pro Gly Glu Leu Gly Ile Phe Ile His Glu Pro Ile Ile
        355                 360                 365
Ala Ala Leu Glu Ala Gln Asn Glu Ala Lys Gly Ile Met Asp Gly Arg
    370                 375                 380
Gln Leu Ala Val Ser Phe Ser Leu Leu Arg Glu Asn Ser Leu Tyr Trp
385                 390                 395                 400
Asn Tyr Tyr Ile Asp Ser Tyr Leu Lys Gly Gln Ser Pro Val Ala Phe
                405                 410                 415
Asp Leu Leu His Trp Asn Ser Asp Ser Thr Asn Val Ala Gly Lys Thr
            420                 425                 430
His Asn Ser Leu Leu Arg Arg Leu Tyr Leu Glu Asn Gln Leu Val Lys
        435                 440                 445
Gly Glu Leu Lys Ile Arg Asn Thr Arg Ile Asp Leu Gly Lys Val Lys
    450                 455                 460
Thr Pro Val Leu Leu Val Ser Ala Val Asp Asp His Ile Ala Leu Trp
```

```
            465                 470                 475                 480
Gln Gly Thr Trp Gln Gly Met Lys Leu Phe Gly Gly Glu Gln Arg Phe
                    485                 490                 495

Leu Leu Ala Glu Ser Gly His Ile Ala Gly Ile Ile Asn Pro Pro Ala
                500                 505                 510

Ala Asn Lys Tyr Gly Phe Trp His Asn Gly Ala Glu Ala Glu Ser Pro
            515                 520                 525

Glu Ser Trp Leu Ala Gly Ala Thr His Gln Gly Gly Ser Trp Trp Pro
        530                 535                 540

Glu Met Met Gly Phe Ile Gln Asn Arg Asp Glu Gly Ser Glu Pro Val
545                 550                 555                 560

Pro Ala Arg Val Pro Glu Gly Leu Ala Pro Ala Pro Gly His Tyr
                565                 570                 575

Val Lys Val Arg Leu Asn Pro Val Phe Ala Cys Pro Thr Glu Glu Asp
                580                 585                 590

Ala Ala

<210> SEQ ID NO 3
<211> LENGTH: 134
<212> TYPE: PRT
<213> ORGANISM: Aeromonas caviae

<400> SEQUENCE: 3

Met Ser Ala Gln Ser Leu Glu Val Gly Gln Lys Ala Arg Leu Ser Lys
1               5                   10                  15

Arg Phe Gly Ala Ala Glu Val Ala Ala Phe Ala Ala Leu Ser Glu Asp
                20                  25                  30

Phe Asn Pro Leu His Leu Asp Pro Ala Phe Ala Ala Thr Thr Ala Phe
            35                  40                  45

Glu Arg Pro Ile Val His Gly Met Leu Leu Ala Ser Leu Phe Ser Gly
        50                  55                  60

Leu Leu Gly Gln Gln Leu Pro Gly Lys Gly Ser Ile Tyr Leu Gly Gln
65                  70                  75                  80

Ser Leu Ser Phe Lys Leu Pro Val Phe Val Gly Asp Glu Val Thr Ala
                85                  90                  95

Glu Val Glu Val Thr Ala Leu Arg Glu Asp Lys Pro Ile Ala Thr Leu
            100                 105                 110

Thr Thr Arg Ile Phe Thr Gln Gly Gly Ala Leu Ala Val Thr Gly Glu
        115                 120                 125

Ala Val Val Lys Leu Pro
        130

<210> SEQ ID NO 4
<211> LENGTH: 158
<212> TYPE: PRT
<213> ORGANISM: Cupriavidus necator

<400> SEQUENCE: 4

Met Arg Thr Ile Ala Ser Leu Glu Glu Leu Glu Gly Leu Gln Gly Gln
1               5                   10                  15

Glu Val Ala Val Ser Asp Trp Ile Glu Val Thr Gln Gln Gln Val Asn
                20                  25                  30

Gln Phe Ala Asp Ala Thr Gly Asp His Gln Trp Ile His Ile Asp Val
            35                  40                  45

Glu Arg Ala Lys Lys Glu Ser Pro Tyr Gly Gly Pro Ile Ala His Gly
        50                  55                  60
```

```
Phe Leu Thr Leu Ser Leu Pro Lys Phe Met His Asn Ala Leu His
 65                  70                  75                  80

Met Pro Ser Lys Ile Gly Val Asn Tyr Gly Leu Asn Arg Val Arg Phe
                 85                  90                  95

Thr Ala Pro Val Pro Val Gly Ser Lys Leu Arg Ala Arg Ile Lys Leu
            100                 105                 110

Leu Lys Val Glu Arg Leu Asp Pro Leu Pro Lys Ser Pro Glu Leu Val
        115                 120                 125

Gly Ala Gln Ser Thr Trp Glu Val Thr Val Glu Arg Glu Gly Ser Asp
    130                 135                 140

Arg Pro Val Cys Val Ala Glu Ser Ile Thr Arg Arg Tyr Gly
145                 150                 155
```

<210> SEQ ID NO 5
<211> LENGTH: 151
<212> TYPE: PRT
<213> ORGANISM: Cupriavidus necator

<400> SEQUENCE: 5

```
Met Lys Thr Tyr Glu Asn Ile Ala Asp Leu Gln Pro Leu Val Gly Glu
  1               5                  10                  15

Val Ile Gly Thr Ser Glu Trp Leu Ala Leu Asp Gln Ala Arg Ile Asn
                 20                  25                  30

Thr Phe Ala Asp Ala Thr Gly Asp His Gln Trp Ile His Val Asp Val
             35                  40                  45

Glu Arg Ala Lys Asn Gly Pro Phe Gly Ala Pro Ile Ala His Gly Phe
         50                  55                  60

Leu Thr Leu Ser Leu Leu Pro Ala Phe Thr His Ser Ala Tyr Arg Ile
 65                  70                  75                  80

Arg Asn Ser Ser Thr Gly Val Asn Tyr Gly Leu Asp Lys Val Arg Phe
                 85                  90                  95

Pro Ala Pro Val Pro Val Asp Ser Leu Leu Arg Ala Gln Phe Lys Leu
            100                 105                 110

Met Ser Tyr Glu Ala Leu Glu Asn Gly Gly Ala Gln Phe Lys Val Glu
        115                 120                 125

Met Met Val Glu Arg Gln Gly Gly Ser Lys Pro Val Cys Ile Ala Glu
    130                 135                 140

Ser Ile Leu Arg Arg Phe Pro
145                 150
```

<210> SEQ ID NO 6
<211> LENGTH: 901
<212> TYPE: PRT
<213> ORGANISM: Yarrowia lipolytica

<400> SEQUENCE: 6

```
Met Ser Gly Glu Leu Arg Tyr Asp Gly Lys Val Val Ile Val Thr Gly
  1               5                  10                  15

Ala Gly Gly Gly Leu Gly Lys Ala Tyr Ala Leu Phe Tyr Gly Ser Arg
                 20                  25                  30

Gly Ala Ser Val Val Val Asn Asp Leu Gly Gly Asp Phe Lys Gly Asp
             35                  40                  45

Gly Ala Gln Ala Gly Ser Gly Lys Arg Val Ala Asp Val Val Asp
         50                  55                  60

Glu Ile Val Ser Lys Gly Gly Lys Ala Val Ala Asn Tyr Asp Ser Val
 65                  70                  75                  80
```

-continued

```
Glu Asn Gly Asp Lys Ile Val Glu Thr Ala Val Lys Ala Phe Gly Ser
                85                  90                  95
Val His Ile Val Ile Asn Asn Ala Gly Ile Leu Arg Asp Ile Ser Phe
            100                 105                 110
Lys Lys Met Thr Asp Lys Asp Trp Asp Leu Val Tyr Lys Val His Val
            115                 120                 125
Phe Gly Ala Tyr Lys Val Thr Arg Ala Ala Trp Pro Tyr Phe Arg Lys
    130                 135                 140
Gln Lys Tyr Gly Arg Val Ile Ser Thr Ser Ser Ala Ala Gly Leu Tyr
145                 150                 155                 160
Gly Asn Phe Gly Gln Thr Asn Tyr Ser Ala Ala Lys Leu Ala Leu Val
                165                 170                 175
Gly Phe Gly Glu Thr Leu Ala Lys Glu Gly Ala Lys Tyr Asn Ile Thr
            180                 185                 190
Ser Asn Val Ile Ala Pro Leu Ala Ala Ser Arg Met Thr Glu Thr Val
            195                 200                 205
Met Pro Glu Asp Ile Leu Lys Leu Leu Lys Pro Glu Tyr Val Val Pro
    210                 215                 220
Leu Val Gly Tyr Leu Thr His Asp Ser Val Thr Glu Ser Tyr Gly Ile
225                 230                 235                 240
Tyr Glu Val Gly Ala Gly Tyr Met Ala Lys Ile Arg Trp Glu Arg Gly
                245                 250                 255
Asn Gly Ala Val Phe Lys Gly Asp Asp Thr Phe Thr Pro Ser Ala Ile
            260                 265                 270
Leu Lys Arg Trp Asp Glu Val Thr Ser Phe Glu Ser Pro Thr Tyr Pro
        275                 280                 285
Asn Gly Pro Ala Asp Phe Phe Lys Tyr Ala Glu Glu Ser Val Lys Arg
290                 295                 300
Pro Glu Asn Pro Gln Gly Pro Thr Val Ser Phe Lys Asp Gln Val Val
305                 310                 315                 320
Ile Val Thr Gly Ala Gly Ala Gly Ile Gly Arg Ala Tyr Ser His Leu
                325                 330                 335
Leu Ala Lys Leu Gly Ala Lys Val Val Asn Asp Phe Gly Asn Pro
            340                 345                 350
Gln Lys Val Val Asp Glu Ile Lys Ala Leu Gly Gly Ile Ala Val Ala
    355                 360                 365
Asp Lys Asn Asn Val Ile His Gly Glu Lys Val Val Gln Thr Ala Ile
370                 375                 380
Asp Ala Phe Gly Ala Val His Ala Val Val Asn Asn Ala Gly Ile Leu
385                 390                 395                 400
Arg Asp Lys Ser Phe Ala Asn Met Asp Asp Glu Met Trp Gln Leu Ile
                405                 410                 415
Phe Asp Val His Leu Asn Gly Thr Tyr Ser Val Thr Lys Ala Ala Trp
            420                 425                 430
Pro His Phe Leu Lys Gln Lys Tyr Gly Arg Val Ile Asn Thr Thr Ser
            435                 440                 445
Thr Ser Gly Ile Tyr Gly Asn Phe Gly Gln Ala Asn Tyr Ser Ala Ala
    450                 455                 460
Lys Ala Gly Ile Leu Gly Phe Ser Arg Ala Leu Ala Arg Glu Gly Glu
465                 470                 475                 480
Lys Tyr Asn Ile Leu Val Asn Thr Ile Ala Pro Asn Ala Gly Thr Ala
                485                 490                 495
```

```
Met Thr Ala Ser Val Phe Thr Glu Glu Met Leu Glu Leu Phe Lys Pro
                500                 505                 510

Asp Phe Ile Ala Pro Ile Thr Val Leu Leu Ala Ser Asp Gln Ala Pro
            515                 520                 525

Val Thr Gly Asp Leu Phe Glu Thr Gly Ser Ala Trp Ile Gly Gln Thr
        530                 535                 540

Arg Trp Gln Arg Ala Gly Gly Lys Ala Phe Asn Thr Lys Lys Gly Val
545                 550                 555                 560

Thr Pro Glu Met Val Arg Asp Ser Trp Ala Lys Ile Val Asp Phe Asp
                565                 570                 575

Asp Gly Asn Ser Thr His Pro Thr Thr Pro Ser Glu Ser Thr Thr Gln
            580                 585                 590

Ile Leu Glu Asn Ile Phe Asn Val Pro Asp Glu Glu Val Glu Glu Thr
        595                 600                 605

Ala Leu Val Ala Gly Pro Gly Gly Pro Gly Ile Leu Asn Lys Glu Gly
    610                 615                 620

Glu Pro Phe Asp Tyr Thr Tyr Thr Tyr Arg Asp Leu Ile Leu Tyr Asn
625                 630                 635                 640

Leu Gly Leu Gly Ala Lys Ala Asn Glu Leu Lys Tyr Val Phe Glu Gly
                645                 650                 655

Asp Asp Asp Phe Gln Thr Val Pro Thr Phe Gly Val Ile Pro Tyr Met
            660                 665                 670

Gly Gly Leu Ile Thr Thr Asn Tyr Gly Asp Phe Val Pro Asn Phe Asn
        675                 680                 685

Pro Met Met Leu Leu His Gly Glu Gln Tyr Leu Glu Ile Arg Gln Trp
    690                 695                 700

Pro Ile Pro Thr Asn Ala Thr Leu Glu Asn Lys Ala Lys Val Ile Asp
705                 710                 715                 720

Val Val Asp Lys Gly Lys Ala Ala Leu Leu Val Thr Ala Thr Thr Thr
                725                 730                 735

Thr Asn Lys Glu Thr Gly Glu Glu Val Phe Tyr Asn Glu Ser Ser Leu
            740                 745                 750

Phe Ile Arg Gly Ser Gly Gly Phe Gly Gly Lys Ser Thr Gly Thr Asp
        755                 760                 765

Arg Gly Ala Ala Thr Ala Ala Asn Lys Pro Pro Ala Arg Ala Pro Asp
    770                 775                 780

Phe Val Lys Glu Ile Lys Ile Gln Glu Asp Gln Ala Ala Ile Tyr Arg
785                 790                 795                 800

Leu Ser Gly Asp Tyr Asn Pro Leu His Ile Asp Pro Ala Phe Ala Ala
                805                 810                 815

Val Gly Asn Phe Asp Arg Pro Ile Leu His Gly Leu Cys Ser Phe Gly
            820                 825                 830

Val Ser Gly Lys Ala Leu Tyr Asp Gln Phe Gly Pro Phe Lys Asn Ala
        835                 840                 845

Lys Val Arg Phe Ala Gly His Val Phe Pro Gly Glu Thr Leu Lys Val
    850                 855                 860

Glu Gly Trp Lys Glu Gly Asn Lys Val Ile Phe Gln Thr Lys Val Val
865                 870                 875                 880

Glu Arg Gly Thr Thr Ala Ile Ser Asn Ala Ala Ile Glu Leu Phe Pro
                885                 890                 895

Lys Asp Ala Lys Leu
            900
```

<210> SEQ ID NO 7
<211> LENGTH: 1185
<212> TYPE: DNA
<213> ORGANISM: Cupriavidus necator

<400> SEQUENCE: 7

```
atgacgcgtg aagtggtagt ggtaagcggt gtccgtaccg cgatcgggac ctttggcggc      60
agcctgaagg atgtggcacc ggcggagctg ggcgcactgg tggtgcgcga ggcgctggcg     120
cgcgcgcagg tgtcgggcga cgatgtcggc cacgtggtat tcggcaacgt gatccagacc     180
gagccgcgcg acatgtatct gggccgcgtc gcggccgtca acggcggggt gacgatcaac     240
gcccccgcgc tgaccgtgaa cgcctgtgc ggctcgggcc tgcaggccat tgtcagcgcc     300
gcgcagacca tcctgctggg cgataccgac gtcgccatcg gcggcggcgc ggaaagcatg     360
agccgcgcac cgtacctggc gccggcagcg cgctgggggcg cacgcatggg cgacgccggc     420
ctggtcgaca tgatgctggg tgcgctgcac gatcccttcc atcgcatcca catgggcgtg     480
accgccgaga atgtcgccaa ggaatacgac atctcgcgcg cgcagcagga cgaggccgcg     540
ctggaatcgc accgccgcgc ttcggcagcg atcaaggccg gctacttcaa ggaccagatc     600
gtcccggtgg tgagcaaggg ccgcaagggc gacgtgacct cgacaccga cgagcacgtg     660
cgccatgacg ccaccatcga cgacatgacc aagctcaggc cggtcttcgt caaggaaaac     720
ggcacggtca cggccggcaa tgcctcgggc ctgaacgacg ccgccgccgc ggtggtgatg     780
atggagcgcg ccgaagccga gcgccgcggc ctgaagccgc tggcccgcct ggtgtcgtac     840
ggccatgccg cgtggaccc gaaggccatg ggcatcggcc cggtgccggc gacgaagatc     900
gcgctggagc gcgccggcct gcaggtgtcg gacctggacg tgatcgaagc caacgaagcc     960
tttgccgcac aggcgtgcgc cgtgaccaag gcgctcggtc tggacccggc caaggttaac    1020
ccgaacggct cgggcatctc gctgggccac ccgatcggcg ccaccggtgc cctgatcacg    1080
gtgaaggcgc tgcatgagct gaaccgcgtg cagggccgct acgcgctggt gacgatgtgc    1140
atcggcggcg ggcagggcat tgccgccatc ttcgagcgta tctga                    1185
```

<210> SEQ ID NO 8
<211> LENGTH: 1179
<212> TYPE: DNA
<213> ORGANISM: Cupriavidus necator

<400> SEQUENCE: 8

```
atgaacgaag cagtcatcgt atccaccgcg cggaccccgc tggccaagag ctggaagggc      60
gccttcaaca tgacccacgg cgccacgctc ggcggtcatg ccgtccagca cgccattgcc     120
cgcgccaaga tcgaggccgc cgaagtggaa gacgtgctga tgggctgcgc caacccggaa     180
ggtgccaccg cgccaacat cgcacgccag atcgcactgc gcgccggctg cccggtgacc     240
gtgcccggcg ccaccgtcaa ccgcttctgc tcgtccggcc tgcagaccat cgccatggcc     300
gcgcagcgcg tgatcgctga tgagggcgac atcttcgtcg ccggcggcgt ggaaagcatc     360
tcgtgcgtgc agcaggagat gaaccgccat atggtccagg aaagctggct gctgaagaac     420
aagccggaaa tctactggaa catgctgcag accgccgaga acgtggccaa gcgctacaac     480
atctcgaagg agcgccagga cgagtacggc gtgcgcagca gcaacgcgc cgccgccggg     540
caggaagccg gcaagttcaa ggacgagatc gtgccgatga cggtgctggc gggcgtggcc     600
gacaagtcga ccgccagct ggtgaccaag gaagtcaccg tctccgccga cgagggcatc     660
cgcgccgata ccacgctgga aggcgtctcc aagatccgca gcgcggtgcc gggtggcgtg     720
```

| | |
|---|---|
| atcaccgccg gcaatgcctc gcagttctcg gacggcgctt cggcagcggt ggtgatgaat | 780 |
| gcgcgcgtcg ccgaggcccg cggcctgcag ccgctgggcg tgttccgcgg ctttgccgtg | 840 |
| gctggctgcg agccggacga gatgggtatc ggcccggtct ttgctgtgcc caagctgctg | 900 |
| aagaaggccg gcctgaaggt cgacgacatc ggcctgtggg agctgaacga agccttcgcc | 960 |
| gtgcaggtgc tgtactgcgc cgacacgctc ggcatcccga tggaccggct gaacgtcaac | 1020 |
| ggcggcgcca tcgccgtggg ccaccccctac ggtgtgtcgg gcgcgcgcct ggtcggccat | 1080 |
| gcgctgatcg aaggcaagcg ccgcggcgtc aagtacgtgg tggtgaccat gtgcatcggc | 1140 |
| ggcggccagg gcgcggccgg cctgttcgaa gtgctctga | 1179 |

<210> SEQ ID NO 9
<211> LENGTH: 1182
<212> TYPE: DNA
<213> ORGANISM: Cupriavidus necator

<400> SEQUENCE: 9

| | |
|---|---|
| atgactgacg ttgtcatcgt atccgccgcc cgcaccgcgg tcggcaagtt tggcggctcg | 60 |
| ctggccaaga tcccggcacc ggaactgggt gccgtggtca tcaaggccgc gctggagcgc | 120 |
| gccggcgtca agccggagca ggtgagcgaa gtcatcatgg ccaggtgct gaccgccggt | 180 |
| tcgggccaga accccgcacg ccaggccgcg atcaaggccg gcctgccggc gatggtgccg | 240 |
| gccatgacca tcaacaaggt gtgcggctcg ggcctgaagg ccgtgatgct ggccgccaac | 300 |
| gcgatcatgg cgggcgacgc cgagatcgtg gtggccggcg ccaggaaaaa catgagcgcc | 360 |
| gccccgcacg tgctgccggg ctcgcgcgat ggtttccgca tggcgatgc caagctggtc | 420 |
| gacaccatga tcgtcgacgg cctgtgggac gtgtacaacc agtaccacat gggcatcacc | 480 |
| gccgagaacg tggccaagga atacggcatc acacgcgagg cgcaggatga gttcgccgtc | 540 |
| ggctcgcaga acaaggccga agccgcgcag aaggccggca gtttgacga agagatcgtc | 600 |
| ccggtgctga tccgcagcg caagggcgac ccggtggcct tcaagaccga cgagttcgtg | 660 |
| cgccagggcg ccacgctgga cagcatgtcc ggcctcaagc ccgccttcga caaggccggc | 720 |
| acggtgaccg cggccaacgc ctcgggcctg aacgacggcg ccgccgcggt ggtggtgatg | 780 |
| tcggcggcca aggccaagga actgggcctg accccgctgg ccacgatcaa gagctatgcc | 840 |
| aacgccggtg tcgatcccaa ggtgatgggc atgggcccgg tgccggcctc caagcgcgcc | 900 |
| ctgtcgcgcg ccgagtggac cccgcaagac ctggacctga tggagatcaa cgaggccttt | 960 |
| gccgcgcagg cgctggcggt gcaccagcag atgggctggg acacctccaa ggtcaatgtg | 1020 |
| aacggcggcg ccatcgccat cggccacccg atcgcgcgt cgggctgccg tatcctggtg | 1080 |
| acgctgctgc acgagatgaa gcgccgtgac gcgaagaagg cctggcctc gctgtgcatc | 1140 |
| ggcggcggca tgggcgtggc gctggcagtc gagcgcaaat aa | 1182 |

<210> SEQ ID NO 10
<211> LENGTH: 1197
<212> TYPE: DNA
<213> ORGANISM: Cupriavidus necator

<400> SEQUENCE: 10

| | |
|---|---|
| atgaaacaac tgcaagacgc atatatcgtt gcggccaccc gctcgccgat cggcaaggcc | 60 |
| ccgaagggcg cgttcaagaa cacgcgcccg gacgacctgc tggcaaccat cctgaaggct | 120 |
| gccgtggcgc aggtgccgga cctggacccg aagctgatcg aagacgccat cgtcggctgc | 180 |
| gcgattcctg aggcgcagca gggcctgaac gtggcgcgca tcggtgcgct gctgtcgggc | 240 |

```
ctgcccaata ccgtgggcgg catcaccgtc aaccgcttct gcgcctcggg cgtgagcgcg      300
gtggcgatgg ctgccgaccg catccgcgtg ggcgagtccg acgtgatgat cgccgccggc      360
gtggaatcga tgagcatggt gccgatgatg ggcaactcgc cgtcgatgtc gccggagatc      420
ttcacccgcg acgagaacgt gggcatcgcc tacggcatgg gcctgaccgc cgagaaggtg      480
gcgcagcaat ggcaggtcag ccgcgaggac caggatgcgt tctcgctggc ctcgcaccag      540
aaggccatcg cggcgcagca ggccggcgag ttcaaggacg agatcacgcc gatcgagatc      600
gtcgagcgct ccccggacct cgccagcggc caggtgaacg tgaagtcgcg cacgatctcg      660
ctggacgaag gcccgcgccc ggagacctcg ctggaaggcc tgggcaagct gcgcccggtg      720
tttgccaaca agggcagcgt caccgccggc aacagctcgc agacctccga cggcgccggc      780
gcgctgatcc tggtctcgga aaagatcctc aagcagttca acctggtgcc gctggcgcgc      840
ttcgtctcgt tcgcggtgcg cggcgtgccg cccgagatca tgggcatcgg ccccaaggaa      900
gcgattccgg cggcgctgaa ggctgcgggc ctgacccagg accagcttga ctggatcgaa      960
ctgaacgagg cctttgccgc gcagtcgctg gcggtgatgc gcgacctgca gctggatccg     1020
gccaaggtca accgcatggg cggcgcgatt cgcctgggcc acccgctcgg tgccaccggt     1080
gcgatccgtt cggccacggt ggtgcacgcg ctgcgccgtc acaacctgaa gtacggcatg     1140
gtgaccatgt gcgttggcac gggcatgggc gccgcaggta tcttcgagcg cgtctga       1197
```

<210> SEQ ID NO 11
<211> LENGTH: 70
<212> TYPE: DNA
<213> ORGANISM: Artificial
<220> FEATURE:
<223> OTHER INFORMATION: Artificially muteted promoter derived from
      Escherichia coli

<400> SEQUENCE: 11

```
caggctttac acttatgctt ccggctcgta tgttgtgtgg aattgtgagc ggataacaat       60
ttcacacagg                                                             70
```

<210> SEQ ID NO 12
<211> LENGTH: 842
<212> TYPE: DNA
<213> ORGANISM: Cupriavidus necator

<400> SEQUENCE: 12

```
gcgcgcattt aaatcacctg gcagggcatg aagctgtttg gcggggagca gcgcttcctc       60
ctggcggagt ccggccacat cgccggcatc atcaacccgc cggccgccaa caagtacggc      120
ttctggcaca acggggccga ggccgagagc ccggagagct ggctggcagg ggcgacgcac      180
cagggcggct cctggtggcc cgagatgatg ggctttatcc agaaccgtga cgaagggtca      240
gagcccgtcc ccgcgcgggt cccggaggaa gggctggccc cgcccccgg ccactatgtc       300 aaggtgcggc tcaaccccgt gtttgcctgc caacagagg aggacgccgc atgacgcttg      360
catgagtgcc ggcgtgcgtc atgcacggcg ccggcaggcc tgcaggttcc ctcccgtttc      420
cattgaaagg actacacaat gactcagcgc attgcgtatg tgaccggcgg catgggtggt      480
atcggaaccg ccatttgcca gcggctggcc aaggatggct tcgtgtggt ggccggttgc       540 ggccccaact cgccgcgccg cgaaaagtgg ctggagcagc agaaggccct gggcttcgat      600
ttcattgcct cggaaggcaa tgtggctgac tgggactcga ccaagaccgc attcgacaag      660
gtcaagtccg aggtcggcga ggttgatgtg ctgatcaaca acgccggtat cacccgcgac      720
```

```
gtggtgttcc gcaagatgac ccgcgccgac tgggatgcgg tgatcgacac caacctgacc     780
tcgctgttca acgtcaccaa gcaggtgatc gacggcatgg ccgaccgtat ttaaatgcgc     840
gc                                                                   842
```

<210> SEQ ID NO 13
<211> LENGTH: 1009
<212> TYPE: DNA
<213> ORGANISM: Cupriavidus necator

<400> SEQUENCE: 13

```
gcgcgcattt aaatggagtt ccagaccctg ctcgacttta tcgccgaagc cgaactggac      60
cgcgtcggct gcttcgccta ctcgccggtg agggcgcca ccgccaatga cctgccgggc     120
gcgctgcccg acgaggtgcg cgaggaacgc gcgcccgct tcatggaagt ggccgaagag     180
gtctcggcgc gccgcctgca gcgcaaggtc ggccagaccc tgcgcgtgct ggtggacgag     240
gtcaaccagg atggcggcat cggccgttcg tccgcggatg cgccgaaat cgacggcctc     300 gtctatatcg cgccgccgga acgccacgcc cagcgctatc gcgccggcga ttcgtcgac     360 gtgaagatca ccgcgccga tggccacgac ctgtggggcg cggtctgaaa cgggttgatt     420
aggtaaaagt acgctcgttc gatttcgtcc gcgtcccgct atactgtgcg gtgcaacata     480
acctcatgga gacaaagtcg gttagccttg cgccttgctt cgctgacgaa gaacctctgc     540
gcgctcggcc tggccgccgt gctcgcgctg gcgggcacgg cgcaggcagc gccggcgacc     600
gagctgtcga ccggcccggt taacaccggg ccagccggcg gcgaaggcct gggcatcaac     660
caggccattc gcgacggcga agcccggcgc ggcggcacct cgctttccac tggcgcgcca     720 aaaccctgg cgccgcggcc ggaatatgcg tcgctgccgg tctacgtcgg caaggtcggc     780
gaccagccgg tgcggctgcg cctgggcccc aagcctgacg agcgcgacag cgtgcgtggc     840
gaatacgccg ccgtggcgc cggtgtgcgc ctgctggcag gcgagtggga ggacggcgcc     900
ttcctgatgg aggagtccga cgacggcacc cgcgtatcgg gcaactggga aggcagcatc     960
gacgccagcg gcgccgtgcg cggcacctgg accgaattta aatgcgcgc                1009
```

<210> SEQ ID NO 14
<211> LENGTH: 829
<212> TYPE: DNA
<213> ORGANISM: Cupriavidus necator

<400> SEQUENCE: 14

```
gcgcgcattt aaattgcatg cgggcttgca cgtgccgcat gcgcggctgg tgatccgcaa      60
gggccaccat gccgacgtgg acagctactc cgccttcctg gaggcggacc gcaccacgcg     120
caccgggctg gccggctacc tgcgcgagca tggcgtcagg cgcgtgttct gcgcgggtct     180
ggcgacggac tactgcgtgg cctggagcgc gctcgatgca cgcgccgcgg gcttcgcggc     240
cgcggtgatc gaggatgcct gccgcgccat cgacctggaa gggtcgctgg ccaaagcatg     300
gcaggacctc ggcgccgccg gcgttgcgcg cgtcacgtcc gctgaactgc tcaagggcca     360
gggctgaacc gaaccaccga actgaacgac acaagagaat ccgaggagca agacatgtcg     420
gctgcgggca ccgcgcgggc cacgcccgcc gacatgctcg cctggggccg ggaggtgctg     480
gccagccagc ccttctcggt cctggtcggc accgaactgg cggcgttgtc gccgggcaag     540
gctgagttgc gcctgccgat ccgtcaggac ctgcggcagc agcacggctt cctgcacggc     600
ggcgtggtca gctacctggc cgacaatgcg ctgacctacg cgggcggcgc ggccatggcg     660
```

```
gtgccggtcg tgacatccga gtacaagatc aactacgtgc gcccggcgat cggcgagctg      720
ctggtcgccc gcgccgaatg cgtcagcgcc ggccgccagc aggcggtggt gcgctgcgac      780
gtgtacgtcg tcagggatgg cgaggagagg ctctgattta aatgcgcgc                  829

<210> SEQ ID NO 15
<211> LENGTH: 3038
<212> TYPE: DNA
<213> ORGANISM: Aeromonas caviae

<400> SEQUENCE: 15
gcgcgcattt aaatccggac cttcgtgcgg ctcaagcccc agcacgtcgc cgggcagcga       60
aaaacccgtt acctgccgcc agcccagcgg cgattcatag acctgcttgg cgctgccatg      120
gcgcagcggg tagaccgtca gcgcagggcg ccctggcga aacacatgct cgccggtgcg       180
cacctctacc agctccggct gcagcgccat cggcgcgtgc ggcaggggg cttgtggccc       240 ggcattgtgg caaacgtggc gaaagaggca gagcaggcag gctggggcgc cgctgtccgg      300
catggtgtca ttgtcctccg gtgacgatgg ccaagtataa aacgccggca acgcaagcca      360
tctcgctgcg atctgcattc tttcgtatgg ctggtttaaa aatttcgcat tacggggcg       420 aggctcgttg cgtttgtgcc ataagcgcgg gagcacgccg gcgggcgtaa tgcggattgt      480
gatatgctgc aacgcaacaa taaaggcata ggaggagatc gcgtcacacg atcaggagtc      540
ctccaattgg cgcaacgcaa ttaatgtgag ttagctcact cattaggcac cccaggcttt      600
acacttatgc ttccggctcg tatgttgtgt ggaattgtga gcggataaca atttcacaca      660
ggaaacaatt gcacgtgcag agagacaatc aaatcatgag ccaaccatct atggcccgc       720 tgttcgaggc cctggcccac tacaatgaca agctgctggc catggccaag gcccagacag      780
agcgcaccgc ccaggcgctg ctgcagacca atctggacga tctgggccag gtgctggagc      840
agggcagcca gcaaccctgg cagctgatcc aggcccagat gaactggtgg caggatcagc      900
tcaagctgat gcagcacacc ctgctcaaaa gcgcaggcca gccgagcgag ccggtgatca      960
ccccggagcg cagcgatcgc cgcttcaagg ccgaggcctg gagcgaacaa cccatctatg     1020
actacctcaa gcagtcctac ctgctcaccg ccaggcacct gctggcctcg gtggatgccc     1080
tggagggcgt cccccagaag agccgggagc ggctgcgttt cttcacccgc cagtacgtca     1140
gcgccatggc ccccagcaac ttcctggcca ccaaccccga gctgctcaag ctgaccctgg     1200
agtccggcgg ccagaacctg gtgcgcggac tggccctctt ggccgaggat ctggagcgca     1260
gcgccgatca gctcaacatc cgcctgaccg acgaatccgc cttcgagctc gggcgggatc     1320
tggccctgac cccgggccgg gtggtgcagc gcaccgagct ctatgagctc attcagtaca     1380
gcccgactac cgagacggtg ggcaagacac ctgtgctgat agtgccgccc ttcatcaaca     1440
agtactacat catggacatg cggccccaga actccctggt cgcctggctg gtcgcccagg     1500
gccagacggt attcatgatc tcctggcgca acccgggcgt ggcccaggcc caaatcgatc     1560
tcgacgacta cgtggtggat ggcgtcatcg ccgccctgga cggcgtggag gcggccaccg     1620
gcgagcggga ggtgcacggc atcggctact gcatcggcgg caccgccctg tcgctcgcca     1680
tgggctggct ggcggcgcgg cgccagaagc agcgggtgcg caccgccacc ctgttcacta     1740
ccctgctgga cttctcccag cccggggagc ttggcatctt catccacgag cccatcatag     1800
cggcgctcga ggcgcaaaat gaggccaagg gcatcatgga cgggcgccag ctggcggtct     1860
ccttcagcct gctgcgggag aacagcctct actggaacta ctacatcgac agctacctca     1920
agggtcagag cccggtggcc ttcgatctgc tgcactggaa cagcgacagc accaatgtgg     1980
```

-continued

```
cgggcaagac ccacaacagc ctgctgcgcc gtctctacct ggagaaccag ctggtgaagg    2040
gggagctcaa gatccgcaac acccgcatcg atctcggcaa ggtgaagacc cctgtgctgc    2100
tggtgtcggc ggtggacgat cacatcgccc tctggcaggg cacctggcag ggcatgaagc    2160
tgtttggcgg ggagcagcgc ttcctcctgg cggagtccgg ccacatcgcc ggcatcatca    2220
acccgccggc cgccaacaag tacggcttct ggcacaacgg ggccgaggcc gagagcccgg    2280
agagctggct ggcaggggcg acgcaccagg gcggctcctg gtggcccgag atgatgggct    2340
ttatccagaa ccgtgacgaa gggtcagagc ccgtccccgc gcgggtcccg gaggaagggc    2400
tggcccccgc ccccggccac tatgtcaagg tgcggctcaa ccccgtgttt gcctgcccaa    2460
cagaggagga cgccgcatga gcctgacctg ccggcctggt tcaaccagtc ggcagccgac    2520
tagtagtcgg gcagcaccaa tgcgcatcaa gcgcgcacaa gtaaagggag ggcgcctgcc    2580
ctcccttttt ccttgcagca gccgcgtcag ccgcgcgagc ggtccttgac gaacagcgca    2640
gtcaccatgc ccagcacgca cagcgcgacc acatagtggg ccggtgccag cggatcctgc    2700
ttcagcatca gcgtgacgac catcggcgtc agcccgccga agatcgcata cgacacgttg    2760
tacgagaatg acaggcccga gaagcgcacc tgcgccggga acgcattgac cagcacgaac    2820
ggcaccgcgc cgatggtgcc gaccaggaag ccggtcagcg catagagcgg cagcagcagg    2880
tcggggcggg tgaagatcgt cgtgtagaac atataggcgc agatggccag cagcaggccg    2940
ccgacgaaca gcgtgcggcg cgcaccgatg cggtcggcta atgcgccgga gacgacacag    3000
ccgatcgtca ggcacagcgt ggcgatttaa atgcgcgc    3038
```

<210> SEQ ID NO 16
<211> LENGTH: 828
<212> TYPE: DNA
<213> ORGANISM: Cupriavidus necator

<400> SEQUENCE: 16

```
gcgcgcattt aaatgccgtc cgacaagatc gtcttcaacg tgcacgagct gctgtacgtg      60
gcgcagaacg aagtgcgcgc gctggccagc gccggctacc gcgcgccgct gccgacgctg     120
gtcccggtgg ccggccgctc gggcattgcc accatcaagg catcgctggt caatatgcgc     180
gacggcggct ttatctcgac gcacgacttc ctgatcgcca gccgcatcgc cgaggcggtg     240
tgcggcggcg acgtcgaggc cggctcgctg gtgagcgagg actggctgct ggcgctggag     300
cgcaaggcct ttgtcgacct gctcggcacc ggcaagacgc aggagcgcat catgggcatg     360
ctgcagaccg gcaagccggt gcgtaactaa cagggcaagc gaggaaccga catcacgcgc     420
ctgcgggacg gtccctcggg actgtcccgc ccttctgcat caggtgaaga aagcagtaac     480
cgggggctgc cgcccgcgac gcgggtcacc aggtagggag gagacaataa tatgcaggag     540
acagccatcc tggccgatgc cgcgtgcgat ctgccgcgcg acgtcatggc ccagctgaag     600
gtccacacga ttccgttccg catccgcgcg ggcgaacact ttgtcgccga tacgcgcgat     660
gaagacgcgc tgcccacgct ctaccagcaa tacctgatcg gccgccagga ccactacgcc     720
gaatcgatcc gctgctcga gcgcgagctg aagaacacc tgctgcgcaa cgtggtggcc     780
cactgcgacc gcgccatcct cttcaccatt gccaatttaa atgcgcgc                 828
```